United States Patent
Chai et al.

(10) Patent No.: US 8,748,373 B2
(45) Date of Patent: Jun. 10, 2014

(54) HEPATITIS B VIRUS COMPOSITIONS AND METHODS OF USE

(75) Inventors: Ning Chai, Philadelphia, PA (US); John M. Taylor, Cheltenham, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 1158 days.

(21) Appl. No.: 12/526,759

(22) PCT Filed: Feb. 20, 2008

(86) PCT No.: PCT/US2008/002236
§ 371 (c)(1),
(2), (4) Date: Jul. 7, 2011

(87) PCT Pub. No.: WO2008/103380
PCT Pub. Date: Aug. 28, 2008

(65) Prior Publication Data
US 2011/0257080 A1    Oct. 20, 2011

Related U.S. Application Data

(60) Provisional application No. 60/902,542, filed on Feb. 21, 2007, provisional application No. 60/902,722, filed on Feb. 22, 2007, provisional application No. 60/902,765, filed on Feb. 22, 2007.

(51) Int. Cl.
*A61K 38/00* (2006.01)
*A01N 37/18* (2006.01)
*A61P 1/16* (2006.01)
*A61P 31/12* (2006.01)
*A61K 38/16* (2006.01)
*A61K 39/00* (2006.01)
*C07K 5/00* (2006.01)
*C07K 7/00* (2006.01)
*C07K 16/00* (2006.01)
*C07K 17/00* (2006.01)
*C12P 21/08* (2006.01)
*C12N 7/00* (2006.01)
*C12N 7/01* (2006.01)

(52) U.S. Cl.
USPC ........... 514/4.3; 514/3.7; 514/21.2; 514/21.3; 424/178.1; 424/183.1; 530/324; 530/387.1; 530/387.3; 435/235.1

(58) Field of Classification Search
None
See application file for complete search history.

(56) References Cited

U.S. PATENT DOCUMENTS

2002/0032307 A1* 3/2002 Tong et al. .................... 530/350
2004/0137016 A1* 7/2004 Moon et al. ................ 424/227.1

FOREIGN PATENT DOCUMENTS

WO    WO2005/087813    9/2005

OTHER PUBLICATIONS

Barrera et al., "Mapping of the Hepatitis B Virus Pre-S1 Domain Involved in Receptor Recognition," J. Virol. 79:9786-9798 (2005).*
Chamow and Ashkenazi, "Immunoadhesins: principles and applications," TIBTECH 14:52-60 (1996).*
Engelke, et al., "Characterization of a Hepatitis B and Hepatitis Delta Virus Receptor Binding Site," Hepatology 43:750-760 (2006).*
Chamow et al., "Immunoadhesions: principles and applications," TIBTECH 14:52-60 (1996).*
Barrera et al., "*Mapping of the Hepatitis B Virus Pre-S1 Domain Involved in Receptor Recognition*," 2005, J Virol 79(15):9786-9798.
Chai et al., "*Immunoadhesins Containing Pre-S domains of Hepatitis B Virus Large Envelope Protein Are Secreted and Inhibit Virus Infection*," 2007, J Virol 81(10):4912-4918.
Chamow et al., "*Immunoadhesins: principles and applications*," 1996, Trends Biotechnol 14(2)52-60.
Engelke et al., "*Characterization of a Hepatitis B and Hepatitis Delta Virus Receptor Binding Site*," 2006, Hepatology 43(4):750-760.
Gripon et al., "*Infection of a human hepatoma cell line by hepatitis B virus*," 2002, Proc Natl Acad Sci USA 99:15655-15660.
Gripon et al., "*Efficient Inhibition of Hepatitis B Virus Infection by Acylated Peptides Derived from the Large Viral Surface Protein*," 2005, J Virol 79:1613-22.
Hong et al., "*Expression and Secretion of Foreign Proteins in Yeast Using the ADH1 Promoter and 97 K Killer Toxin Signal Sequence*," 1998, J Biochem Mol Biol. 31(2):123-129.
Loffler-Mary et al., "*Sequence-Specific Repression of Cotranslational Translocation of the Hepatitis B Virus Envelope Proteins Coincides with Binding of Heat Shock Protein Hsc70*," 1997, Virology, 235(1):144-152.
Prange et al., "*DNA-mediated immunization to hepatitis B virus envelope proteins: preS antigen secretion enhances the humoral response*," 1999, Vaccine 17(7-8):617-623.

* cited by examiner

*Primary Examiner* — James H Alstrum Acevedo
*Assistant Examiner* — Thea D'Ambrosio
(74) *Attorney, Agent, or Firm* — Riverside Law LLP

(57) ABSTRACT

A polypeptide comprising a preS1 region of hepatitis B virus (HBV), or a fragment thereof, and/or the preS2 region of HBV or a fragment thereof, and methods of use to inhibit virus infection are disclosed. A lentivirus comprising hepatitis B virus (HBV) envelope proteins, or a fragment thereof, and/or the L envelope protein of HBV and/or the M envelope protein of HBV or a fragment thereof, and/or the S envelope protein of HBV or a fragment thereof, and methods of use of this lentivirus HBV pseudovirus as a gene therapy to target hepatocytes for the administration of therapeutic agents are also disclosed.

19 Claims, 7 Drawing Sheets

Figure 1:
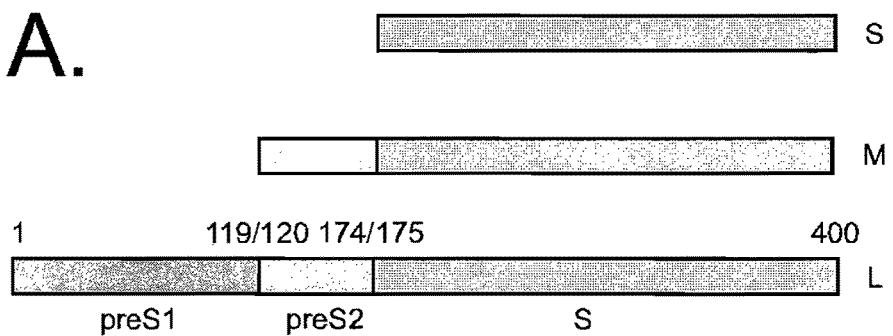
Figure 1:
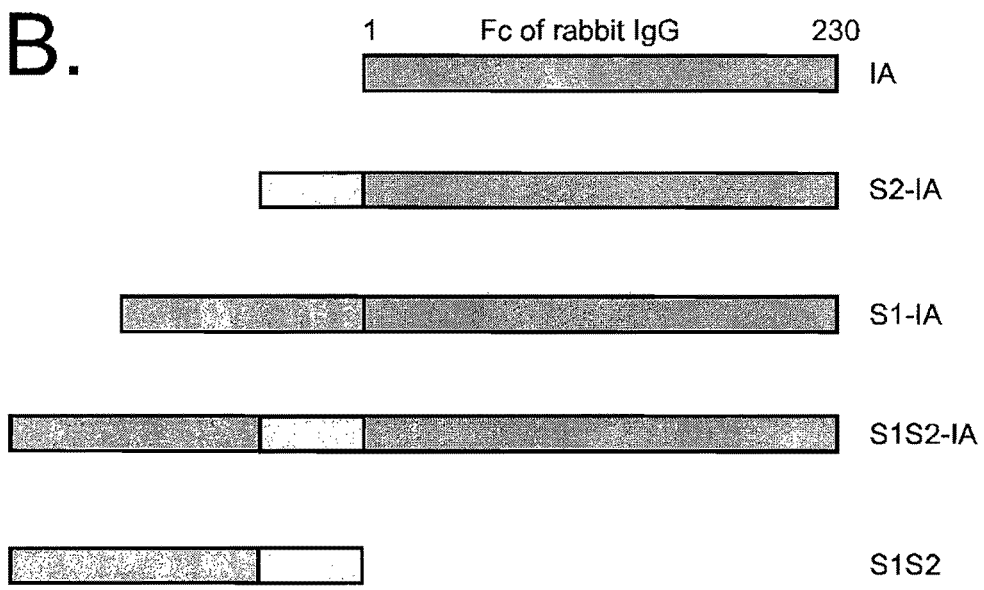

A.

B.

HEPATITIS B VIRUS COMPOSITIONS AND METHODS OF USE

CROSS-REFERENCE TO RELATED APPLICATIONS

The present application is a continuation-in-part of International Patent Application No. PCT/US2008/002236, filed Feb. 20, 2008, which claims priority under 35 U.S.C. §119(e) to U.S. Provisional Application No. 60/902,542, filed Feb. 21, 2007, U.S. Provisional Application No. 60/902,765, filed Feb. 22, 2007, and U.S. Provisional Application No. 60/902,722, filed Feb. 22, 2007, all of which are hereby incorporated by reference in their entirety herein.

STATEMENT REGARDING FEDERALLY SPONSORED RESEARCH OR DEVELOPMENT

This invention was supported in part by funds obtained from the U.S. Government (National Institutes of Health Grant Numbers AI-058269 and CA-06927), and the U.S. Government therefore has certain rights in the invention.

BACKGROUND OF THE INVENTION

Hepatitis B virus (HBV) is the infectious agent that triggers hepatitis B. Chronic HBV affects about 350 million people worldwide. Once an individual is infected, HBV targets the liver eventually causing scarring of the liver (cirrhosis) and liver failure. According to the World Health Organization, HBV is 100 times more infectious than human immunodeficiency virus (HIV) and is readily transmitted through blood and bodily fluids. There is no known cure for HBV, and even with new treatments available, each year it is estimated that 5000 Americans and one million individuals worldwide die from hepatitis's major sequelae: cirrhosis and hepatocellular carcinoma.

HBV, like all other viruses, must first attach to a cell capable of supporting its replication. Viral attachment is mediated via specific envelope proteins expressed on the surface of the virus. These proteins define the virus's tropism. Moreover, the chronic disease is associated with a massively increased risk of primary liver carcinoma which results in about one million deaths each year.

Hepatitis B virus has a small, circular DNA genome with a size of about 3.2 kb. The viral genome carries four genes named the C, S, X, and P genes. The C gene codes for the viral core protein that packages the viral genome and also for a related protein named precore protein. The precore protein is the precursor of the secreted e antigen, which may be important for the establishment of persistent infection following neonatal infection (for a review, see Ou, 1997, J Gastroenterol Hepatol., 12:S178-S187). The S gene codes for three co-carboxy-terminal envelope proteins known as surface antigens or L, M and S envelope proteins (see below). The X gene codes for a transcriptional transactivator, and the P gene codes for the viral DNA polymerase, which is also a reverse transcriptase.

The expression of the HBV genes is regulated by four different promoters and two enhancer elements (Yen, 1993, Semin Virol., 4:33-42). The core promoter regulates the transcription of the precore RNA and the core RNA, the L promoter regulates the expression of the L RNA, the major S promoter regulates the transcription of the M RNA and the major S RNA, and the X promoter regulates the transcription of the X RNA. The precore RNA and the core RNA are larger than the genome length. However, only the latter is used as the mRNA for the synthesis of the viral DNA polymerase (Nassal, et al., 1990, Cell, 63:1357-1363; Ou, et al., 1990, J Virol., 64:4578-4581). The ENI enhancer partially overlaps the X promoter, and the ENII enhancer is located upstream of the core promoter (Guo, et al., 1991, J Virol., 65:6686-6692; Shaul, et al., 1985, EMBO J., 4:427-430; Wang et al., 1990, J Virol, 64:3977-3981; Yee, 1989, Science, 246:658-661; Yuh and Ting, 1990, J Virol., 64:4281-4287). Both enhancers can upregulate the activities of all four HBV gene promoters (Antonucci and Rutter, 1989, J Virol., 63:579-583; Yee, 1989, Science, 246:658-661). Only one of the HBV DNA strands is coding, and therefore the transcription of the HBV genes is unidirectional. All of the HBV RNA transcripts terminate at the same poly(A) site in the viral genome. It has been demonstrated that cis-acting elements as well as the distance between the promoter and the poly(A) site play important roles in determining whether the poly(A) site should be used or bypassed for polyadenylation of the viral RNA (Cherrington et al., 1992, J Virol., 66:7589-7596; Guo et al., 1991, Virology, 181:630-636; Russnak and Ganem, 1990, Genes Dev., 4:764-776). For example, as this site is located less than 200 bp from the core promoter, the C gene transcripts bypass this site the first time and become polyadenylated at this site only after they have circled around the genome once and encounter the site the second time. In contrast, this poly(A) site is located approximately 2 kbp away from the S gene promoters and is therefore used efficiently by the S gene transcripts for polyadenylation when the site is first encountered during transcription. The X promoter is located about 700 bp upstream of the poly(A) site, and therefore the X gene transcripts bypass this poly(A) site with an intermediate efficiency of approximately 50% (Guo et al., 1991, Virology, 181:630-636). This leads to the production of two different X gene transcripts: one with a subgenomic size of 700 nucleotides (nt) and the other with a larger-than-genome size of 3.9 kb (Guo et al., 1991, Virology, 181:630-636).

All three Hepatitis B surface proteins, S, M and L, are also known as Hepatitis B surface antigens (HBsAg). HBsAgs are the earliest indicators of acute hepatitis B, often detectable before symptomatic onset; their expression level remains high in individuals with chronic infection. Within the HBV genome, the region encoding the HBV surface proteins contains three in-frame start sites which share a common termination codon. Because of this, the various HBV surface proteins are all related to each other by a shared region known as the S-domain. The two larger proteins (L and M, respectively) have a C-terminus in common with S. PreS2 is the sequence of M that is unique relative to S. PreS1 is the sequence of L that is unique relative to M. The N terminus of HBV preS1 contains a domain that is considered essential for an interaction between the virus and as yet unidentified host receptor(s) (Barrera, et al., 2005, J. Virol., 79:9786-9798, Engelke, et al., 2006, Hepatology, 43:750-760, Gripon, et al., 2005, J. Virol., 79:1613-1622, Loffler-Mary, et al., 1997, Virology, 235:144-152). This region overlaps with one that can act as an endoplasmic reticulum retention signal (Kuroki, et al., 1989, Mol. Cell. Biol., 9:4459-4466) probably because it interacts with host molecular chaperones (Cho, et al., 2003, J. Virol., 77:2784-2788, Ryu, et al., 2000, J. Virol., 74:110-116).

In addition to acting as HBV surface antigens/proteins, L, M and S can be secreted from infected cells as subviral particles, although L alone can only be released when S is also present (Cheng, et al., 1986, J. Virol., 60:337-344, Persing, et al., 1986, Science, 234:1388-1391). S protein alone is sufficient for N-glycosylation and secretion (Bruss, et al., 1991, Proc. Natl. Acad. Sci., USA 88:1059-1063). All three proteins undergo some level of N- or O-glycosylation prior to release, consistent with their transport through the endoplasmic reticulum (ER) and Golgi apparatus (Gelich, et al., 2005, Hepatitis B, In TOPLEY AND WILSON'S MICROBIOLOGY AND MICROBIAL INFECTIONS, Volume 2, A.S.M. Press, Washington). L is myristoylated at a glycine penultimate to the N-terminal methionine (Persing, et al., 1987, J. Virol., 61:1672-1677). This modification is not essential for assembly but is required for infectivity (Bruss, et al., 1996, Virology, 218:396-399, Gripon, et al., 1995, Virology, 213:292-299). The PreS domains of L can exist in two quite different topological conformations, due to post-translational translocation across the ER membrane (Bruss, et al., 1994, EMBO J., 13:2273-2279, Ostapchuk, et al., 1994, EMBO J., 13:1048-1057, Prange, et al., 1995, EMBO J., 14:247-256). It has been shown that sequences within S act as a signal for PreS2 translocation of M (Eble, et al., 1990, J. Virol., 64:1414-1419). Furthermore, it has been assumed that sequences within S also direct translocation of upstream sequences in the L protein (Lambert, et al., 2001, J. Biol. Chem., 276:22265-22272). Consequently, for L and M it has been presumed that the preS1 and preS2 domains, respectively, do not contain any translocation signal. As a direct test of this interpretation previous studies have attempted to fuse the preS1 plus preS2 domains to a reported protein, and were unable to detect translocation into ER-derived microsomes (Ostapchuk, et al., 1994, EMBO J., 13:1048-1057).

The major antigenic epitope of hepatitis B virus is a highly conserved region spanning 23 amino acid residues and located from amino acid position 124 to 147 of the major surface antigen. This small region designated as the group specific determinant "a" is found in all subtypes and isolates of hepatitis B viral genomes. Its antigenic properties seem due to its proposed double loop structure, to which the vaccine-induced neutralizing antibody binds.

In contrast to random mutations introduced into hepatitis B viral genomes during viral replication by the proof-reading defective reverse transcriptase, mutations induced following vaccination occur mainly in the "a" epitope of the major surface antigen. These mutant viruses are of particular interest since they show reduced affinity to the neutralizing antibody and therefore are able to replicate independently. Among these vaccine-escape mutants, the mutation at amino acid residue 145 (from Glycine to Arginine) in the second loop of the major surface antigen is the most significant because it is stable, results in conformational changes of the "a" epitope and has been reported worldwide in North America, Europe, Japan and Southeast Asia. In Singapore, for example, such mutants are the most frequent variant following vaccination. Twelve infectious variants among 41 breakthroughs have been identified as having an arginine mutation at amino acid residue 145 of the major surface antigen. There is evidence of vertical transmission from one of the 12 variants and this variant has also been associated with active liver disease. Significantly, some of these variants are now found in random asymptomatic adult population.

Hepatitis B e-antigen (HBeAg) is a hepatitis B viral protein secreted by infected hepatocytes directly into the blood only when virus is present. Usually, HBeAg in serum is associated with a high viral titre and active, progressive liver disease. As such, it is used as an indicator of an individual's ability to infect others as well as a marker to monitor efficacy of treatment. Serum HBeAg loss and development of anti-HBe antibody (seroconversion) is associated with amelioration of disease and a reduction in viral load. This also involves normalization of serum aminotransferases as well as improved histology. However, some patients may be HBeAG-negative and be anti-HBe positive yet still have high levels of virus and active disease. The latter are due to the presence of a variant form of the virus that is particularly common in the Middle East and Asia. The most common of these HBeAg mutations results in the introduction of a premature stop codon in the open-reading frame of the precore region of the virus; this leads to a lack of HBeAg secretion into the blood. Patients with precore mutant anti-HBe-positive hepatitis B have lower HBV DNA levels than HBeAg-positive patients, but they still suffer from progressive liver disease.

Hepatitis B is difficult to cure. The aim of current treatment regimens is to enable to patient's immune system to control viral infection by administering therapeutic agents that decrease HBV replication. In addition, current treatment attempts to prevent further liver damage by attenuating hepatic necroinflamation, thereby preventing progression to fibrosis. Interrupting fibrogenesis prevents subsequent progression to cirrhosis and its associated complications, thus improving survival. A typical response to treatment can be classified in three phases: (1) decrease HBV replication as measured by serum HBV-DNA levels; (2) liver necroinflamation diminishes and fibrosis is stabilized, but the risk of viral reactivation persists; (3) if the antiviral effect is sufficient (<100,000 copies of HBV DNA per ml), is maintained and is accompanied by an effective immune response with clearance of infected hepatocytes, HBe seroconversion may occur and the risk of viral reactivation is low. If HBV replication is completely interrupted with stable HBe serovonversion and loss of detectable HBsAg may occur which is associated with complete loss of necroinflamation and no risk of reactivation. This is as close to a cure as can be hoped for.

Five drugs are now licensed to treat chronic hepatitis B infection: conventional interferon alfa-2b (IFN-$\alpha$ 2b), peginterferon alfa-2a, lamivudine, adefovir and entecavir. However, treatment may be ineffective or become so by the emergence of drug resistant virus. Even if successful, drug regimens suffer from such disadvantages as being long-term, expensive and associated with many undesirable side effects. When end-stage liver disease supervenes in chronic HBV infection, liver transplantation is the only alternative, however viral infection persists and infects the graft, significantly shortening both patient and graft survival. In addition, while there is good agreement that combination therapy offers the best hope for an effective future strategy in disease management, improving efficacy of treatment while preventing the development of resistance, all of the combination regimens tried so far have failed to demonstrate efficacy.

After binding of the viral particles to surface molecules of hepatocytes and other cells of hepatic and nonhepatic origin, the virus is transported into the cells and the viral genome is transported into the nucleus. The viral genome, during or after entering the nucleus, is converted to a completely double-stranded supercoiled DNA genome (cccDNA). All viral RNAs are transcribed from the cccDNA. A greater than genome length RNA, the pregenome, is terminally redundant. Subgenomic RNAs are also transcribed, from which the structural and nonstructural proteins are translated.

Phosphorylation and dephosphorylation of the core protein play an important part in the assembly of the nucleocapsid, in DNA synthesis, in the association of the nucleocapsid proteins with the nuclear membrane and their transport into the nucleus, and in nucleocapsid disintegration which is necessary in order to transport the genome into the nucleus. Modifications in the phosphorylation of the nucleocapsid can interfere with the infectivity of the hepadnaviruses and with the infection process. Once DNA synthesis has reached a particular state of maturation, the virus is enveloped. Some of the nucleocapsids migrate to the nuclear membrane and thus provide the necessary increase in the cccDNA copy number.

In recent years, α-interferon produced by genetic engineering has been found useful in the treatment of HBV infections. It is a cytokine with broad antiviral and immunomodulating activity. However, it is effective in only about 33% of the patients, entails considerable side effects, and cannot be administered by the oral route.

A nucleoside derivative, Lamivudine (β-L-2',3'-dideoxy-3'-thiacytidine), also known as thiacytidine (3TC), which has been described by Liotta et al. in U.S. Pat. No. 5,539,116, has been applied with success against HBV infection and approved by the U.S. Food and Drug Administration. It is remarkable for its high efficacy both in HbeAg-positive and HbeAg-negative patients and has few side effects. However, such therapies are associated with an increasing risk of resistance to lamivudine, which can be as high as 45-55% after the second year of treatment (Liaw et al., 2000 Gastroenterology 119: 172-180).

Although rapid decline of HBV DNA and normalization of the alanine transferase activity in serum is found in such treatment, HBV apparently cannot be completely eliminated from the liver under such therapy, so that reactivation of a hepatitis B infection is possible in many cases even after completion of a one-year treatment. Attempts are being made to prevent the above course by extending the treatment to several years, in the hope that HBV could be eliminated completely (Alberti et al., 2002, J Med Virol 67: 458-462).

In recent years considerable effort has been directed at developing safe and effective gene delivery systems and techniques. Viruses, which have evolved efficient mechanisms of delivering genomic packages to a variety of cell types, are particularly attractive candidates.

Vectors derived from retroviruses such as the lentivirus are probably among the most suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Primate lentiviruses, such as HIV and SIV, are distinguished by their use of the CD4 protein as a receptor. They have four main genes coding for virion proteins which are, in order: 5'-gag-pro-pol-env-3'. HIV has additional genes vif, vpr, vpu, tat, rev, and nef, whose products are involved in regulation of synthesis and processing of virus RNA as well as other replicative functions.

The host range of retroviruses including lentiviral vectors can be expanded or altered by a process known as pseudotyping. Pseudotyped lentiviral vectors consist of viral particles bearing glycoproteins (GP) derived from other enveloped viruses. Such particles possess the tropism of the virus from which the GP were derived. Pseudotyping is a process that commonly occurs during viral assembly in cells infected with two or more viruses (Zavada, J. The pseudotypic paradox. J. Gen. Virol. 63:15-24, 1982). HIV-1 has long been known to form pseudotypes by the incorporation of heterologous GPs through phenotypic mixing, allowing an extension of the host range of HIV-1 virions beyond cells that express the CD4 receptor and an appropriate co-receptor.

However, viral pseudotyping is not a straightforward process. Co-expression of a given glycoprotein with a heterologous viral core will not necessarily give rise to highly infectious viral particles. There are examples of restriction of pseudotype formation, notably between GPs and viral cores derived from different retroviral families such as GALV and RD114 lentiviral pseudotypes. In fact, functional associations between viral cores and glycoproteins are unpredictable. An added complexity has made HBV an unlikely candidate for pseudotyping: in contrast to HIV proteins which are assembled on the cell surface, HBV envelope proteins are retained within the cell.

The occurrence of a replicative vaccine-induced HBV mutant and its ability to escape detection using standard reagents is of grave concern because it has resulted in the development of acute hepatitis B in Italy and Singapore. This situation therefore requires the urgent development of specific detection systems, as well as, effective prophylactic vaccines and antiviral agents. Thus, there is a long felt need in the art for efficient and directed means of inhibiting HBV infection and therapies to treat disorders associated thereof.

SUMMARY OF THE INVENTION

The present invention includes a secreted recombinant polypeptide comprising at least 30 contiguous amino acids of the sequence of preS1 region of HBV and does not contain amino acids of the sequence of the S region of HBV. The secreted polypeptide is capable of inhibiting virus infection of hepatocytes. In certain aspects, the virus infection is by HBV. In other aspects, the virus infection is by HBV and HDV.

In one embodiment, the polypeptide comprises 30 contiguous amino acids of the first 30 amino acids of preS1 region of HBV. In another embodiment, the polypeptide comprising the sequence of preS1 is fused to a constant domain sequence of an immunoglobulin. The immunoglobulin is selected from the group consisting of IgG-1, IgG-2, IgG-3, IgG-4, IgA, IgE, IgD, and IgM.

In another embodiment, the polypeptide comprising preS1 is fused to a sequence of preS2 region of HBV, thereby forming a polypeptide designated as S1S2. In certain aspects, the S1S2 polypeptide is further fused to an immunoglobulin sequence.

The invention also includes a method of in vivo inhibition of hepatocyte infection, the method comprising administering an effect amount of a nucleic acid sequence encoding a polypeptide comprising at least 30 contiguous amino acids of the sequence of preS1 region of HBV, wherein the polypeptide is capable of inhibiting virus infection of hepatocytes to an animal in need thereof, further wherein the polypeptide does not contain nucleic acid sequences encoding the S region of HBV.

The invention includes a method of in vivo inhibition of hepatocyte infection, the method comprising administering an effect amount of a secreted polypeptide comprising at least 30 contiguous amino acids of the sequence of preS1 region of HBV, wherein the polypeptide is capable of inhibiting virus infection of hepatocytes to an animal in need thereof, further wherein the polypeptide does not contain amino acids of the sequence of S region of HBV.

The invention also includes an isolated polynucleotide encoding a polypeptide comprising at least 30 contiguous amino acids of the sequence of preS1 region of HBV, wherein the polypeptide is capable of inhibiting virus infection of hepatocytes, further wherein the polypeptide does not contain amino acids of the sequence of the S region of HBV.

The present invention provides a recombinant lentivirus capable of infecting non-dividing cells as well as methods and means for making same. The virus is useful for the in vivo and ex vivo transfer and expression of nucleic acid sequences.

In one embodiment, the lentiviral pseudovirus is capable of infecting hepatocytes. Preferably, the hepatocyte is of human origin. In certain aspects, the pseudovirus expresses an HBV surface protein. The HBV surface protein includes, but is not limited to L, M, and S.

In another embodiment, the lentiviral pseudovirus comprises a nucleotide sequence encoding a therapeutic protein associated with liver disease. In certain aspects, the nucleotide sequence encodes an inhibitor of gene expression for a gene associated with liver disease.

The invention also includes a lentivirial pseudovirus expressing an HBV surface protein, wherein the pseudovirus comprises a nucleotide sequence encoding an inhibitor of gene expression for a conserved target sequence present in HBV. Examples of a conserved target sequence present in HBV is gene C, gene S, gene X, gene P, and the like.

The invention includes a method of producing a lentiviral pseudovirus expressing a Hepatitis B surface protein. In one embodiment, the method comprises transfecting a host cell with a first plasmid comprising a modified HIV genome; and a second plasmid comprising a HBV gene encoding one or more HBV surface proteins; and recovering the recombinant virus. In certain aspects, the method can further comprise a third plasmid encoding a reporter gene.

The invention also includes a method for reducing expression of a target gene in a hepatocyte. In one embodiment, the method comprises introducing into the hepatocyte a lentiviral vector encoding an inhibitor of gene expression for a gene associated with liver disease, wherein the inhibitor causes a detectable decrease in expression of the gene associated with liver disease. In certain aspects, includes a method of expressing a target gene in a hepatocyte, the method comprising introducing into the hepatocyte a lentiviral vector encoding a nucleotide sequence specific for a gene associated with liver disease.

Other features and advantages of the invention will be understood by reference to the drawings, detailed description and examples that follow.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A and 1B is a schematic depicting HBV envelope proteins and construction of an immunoadhesin (IA). FIG. 1A is a representation of L, M, and S, the three HBsAg of the adw2 serotype of HBV. The preS1 and preS2 domains, along with the amino acid numbering are from Genbank AAK58874.1. FIG. 1B shows the Fc region of a rabbit IgG heavy chain and three IA that were constructed as N terminal fusion with HBV preS sequences. Also shown is a protein comprising simply the S1S2 domain.

FIG. 2, comprising FIGS. 2A and 2B is a series of charts depicting Immunoblot detection and quatitation of IA and S1S2 protein. The domains indicated in FIG. 1B were assembled in the expression vector under control of a β-actin promoter. Two days after transfection into 293T cells both media and cell samples, as indicated by “c” and “m” respectively, were examined by immunoblot. In FIG. 2A, the four IA were detected via dye-labeled goat anti-rabbit antibody. In FIG. 2B, the S1S2 protein was detected via S-26, a mouse monoclonal antibody specific for the HBV preS2 domain. In both FIGS. 2A and 2B, hsc70 was detected via a mouse monoclonal antibody.

FIG. 3, comprising FIGS. 3A through 3C, is a series of charts depicting incorporation of $^{3}$H-myristic acid into IA. 293T cells were transfected with vectors that express S1-IA or S1S2-IA, either as a wild type (wt) or mutated (mut) at the two glycines near the N-terminus. After 2 days in the presence of $^{3}$H-myristic acid and reduced serum, the cells were extracted and immuno-selected using protein A-agarose. The selected materials were subjected to polyacrylamide gel electrophoresis and electrotransfer to a nitrocellulose membrane. FIG. 3A shows the detection of $^{3}$H on the membrane. FIG. 3B shows the results when this same filter was then subjected to immunoblot using a dye-labeled goat anti-rabbit antibody to detect IA. FIG. 3C is an immunoblot with a monoclonal antibody Ma18/7, directed at an epitope within the PreS1 region. The amounts of mutated proteins examined were made greater than those for wild type in order to accentuate the fact that the mutated proteins lack detectable $^{3}$H-labelling.

FIG. 4, comprising FIGS. 4A through 4C, is a series of charts depicting the ability of IA and related proteins to inhibit infection by HDV and HBV of primary human hepatocytes. FIG. 4A demonstrates the quantification of IA expressed in 293T cells and secretion thereof into the media. The aliquots of these media were used at three concentrations, in assays for their effect on the ability of HDV to infect primary human hepatocytes. A comparison was made with respect to S1S2, which lacks the IA domain, and a myristoylated synthetic peptide corresponding to the N terminus of HBV ayw PreS1. The concentrations used were 2, 10 and 50 nM, as indicated by progressively darker shades of gray. The vertical axis expresses in arbitrary units the amount of antigenomic HDV RNA per infected cell, as determined by quantitative real-time PCR. Indicated are average values with standard deviation, from independent infections. FIG. 4B depicts demonstrates the role of S1S2-IA on viral replication. S1S2-IA was tested for its effects on HDV replication, and as indicated, for the consequences after a pretreatment of 30 minute, given in addition to the treatment during infection. FIG. 4C shows an experiment carried out in parallel with that of FIG. 4B, except that HDV was replaced by HBV, and the real-time PCR assays were directed HBV RNA.

FIG. 5 is a chart depicting the FACS detection of 293T cells transfected with plasmids coding for HBV surface protein, a modified HIV viral genome, and a LacZ.

FIG. 6 is a photomicrograph of primary cultured human heptocytes expressing LacZ indicative of infection of lentivirus pseudotyped with HBV surface proteins.

FIG. 7 is a series of photomicrographs comparing the HBV lentivirus with the VSV G lentivirus with respect to the infection of primary hepatocytes. Cells used were HuH-7 cells and 293T cells.

DETAILED DESCRIPTION OF THE INVENTION

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a pulmonary surfactant" includes a combination of two or more pulmonary surfactants, and the like.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 5'-ATTGCC-3' and 5'-TATGGC-3' share 50% homology.

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule of the invention typically is a contiguous amino acid sequence comprising the first 30 amino acids of preS1 from HBV. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Pseudotyped virus" as used herein refers to changing the plasmid encoding the expression of an envelope protein thereby changing the host range and tissue tropism of a viral vector.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

The term "therapeutic" as used herein means a treatment and/or prophylaxis. A therapeutic effect is obtained by suppression, remission, or eradication of a disease state associated with liver disease.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes for instance, prevention of HBV propagation to uninfected cells of an organism.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, "vaccination" is intended for prophylactic or therapeutical vaccination. "Therapeutical vaccination" is meant for vaccination of a patient with HBV and/or HDV infection.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "virus" as used herein is defined as a particle consisting of nucleic acid (RNA or DNA) enclosed in a protein coat, with or without an outer lipid envelope, which is capable of replicating within a whole cell.

Description:

A. Compositions Containing HBV Pre-S Domains

The present invention relates to compositions and derivatives thereof that are useful for antiviral therapies against HBV infection. The invention also includes antiviral therapies against HDV infection. In addition, the invention includes compositions and derivatives thereof to inhibit infection of hepatocytes by a subviral agent that utilizes HBV envelope proteins.

The invention is partly based on the discovery that the N terminus of preS1 region of HBV is capable of promoting protein secretion. In addition, when the preS1 region is fused to an Fc domain of an IgG chain (i.e., immunoadhesin ("IA")), the fusion protein can still be secreted. Furthermore, such secreted IA fusion proteins (e.g., S1-IA and S1S2-IA) as well as the secreted free S1S2 region, without any IA fusion, are capable of inhibiting infection of hepatocytes by HBV and/or HDV.

The invention further relates to the discovery that as few as 30 amino acids from the N terminus of preS1 are sufficient to promote secretion, for example secretion of an IA, in a eukaryotic cell. The secreted species, including but not limited to S1-IA, S1S2-IA, and secreted free S1S2 can exhibit direct inhibitory activity against HBV and/or HDV infection and makes it possible to elicit protection against HBV and/or HDV infection.

Preparation of HBV preS Secreted Proteins

The polypeptides of the present invention were designed from the sequence of the preS regions (e.g., preS1 region and preS2 region) from HBV. Accordingly, the invention includes a polypeptide comprising at least 30 contiguous amino acids of the sequence of preS1 region of HBV. In some instances, the polypeptides of the invention are engineered to not contain sequences of the S region of HBV. For example, the polypeptides of the present invention include, but are not limited to S1 (containing preS1 sequences) and S1S2 (containing sequences from preS1 and preS2). Both polypeptides designated as S1 and S1S2 do not contain sequences from the S region of HBV.

The polypeptides of the present invention also encompass fusion proteins comprising a preS region from HBV. For example, the fusion protein can comprise a preS region fused to an Fc region of an IgG (e.g., IA). Using the information provided herein, the preS polypeptides can be produced recombinantly using standard techniques well known to those of skill in the art or produced by a host cell in vivo. For example, the sequences of HBV set forth in Genebank AAK58874.1 can be used to engineer a polypeptide comprising a desired preS region from HBV (e.g., FIG. 1). The nucleic acid sequence may be optimized to reflect particular codon "preferences" for various expression systems according to methods known in the art.

Exemplary, the fragment of the preS region comprises at least 5 amino acids, more exemplary at least 6 amino acids, most exemplary 10, 15 or 20 amino acids. The fragment may include, for example, amino acids 1 to 19, 20 to 39, 40 to 59, 60 to 79, 80 to 99 or 100 to 119 of preS1, or 1 to 19, 20 to 39 or 40 to 55 of preS2. Suitable fragments which may be used in the polypeptides of the invention are described elsewhere herein. Preferred fragments include fragments comprising at least amino acids 1 to 30 of preS1. Other fragments include the combination of preS1 and preS2 sequences.

The invention also includes a fusion protein comprising a preS region. The fusion protein can comprise a desired preS region fused to an Fc region (e.g., IA). Fusion proteins of the invention include, but are not limited to, proteins having diverse components. In general, a fusion protein can be produced by preparing a fused gene comprising a first DNA segment that encodes a region of the preS region of HBV, such as the first 30 amino acid of preS1, to a second DNA segment encoding at least a part of a constant region (e.g., Fc of a mammalian IgG). Each fused gene is assembled in, or inserted into an expression vector. Recipient cells capable of expressing the gene products are then transfected with the genes. The transfected recipient cells are cultured under conditions that permit expression of the incorporated genes and the expressed and secreted fusion proteins are harvested. Alternatively, the expression vector can be administered into a human or animal in need thereof. In this situation, the cells express and secrete the fusion protein in the human or animal.

Immunoadhesins are chimeric antibody-like molecules combining the functional domain(s) of a binding protein (usually a receptor, a cell-adhesion molecule or a ligand) with an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions. In some instances, the fusion protein of the present invention is an immunoadhesin, wherein a preS region is fused to an immunoglobulin sequence.

Immunoadhesins reported in the literature include, for example, fusions of the T cell receptor (Gascoigne et al., 1987, Proc. Natl. Acad. Sci. USA 84:2936-2940); CD4 (Capon et al., 1989, Nature 337: 525-531; Traunecker et al., 1989, Nature 33: 68-70; Zettmeissl et al., 1990, DNA Cell Biol. USA 9: 347-353; Byrn et al., 1990, Nature 344: 667-670; L-seNRG3 (homing receptor) (Watson et al., 1990, J. Cell. Biol. 110: 2221-2229); Watson et al., 1991, Nature 349: 164-167); E-seNRG3, (Mulligan et al., 1993, J. Immunol. 151: 6410-17; Jacob et al., 1995, Biochemistry 34: 1210-1217); P-seNRG3 (Mulligan et al., supra; Hollenbaugh et al., 1995, Biochemistry 34: 5678-84); ICAM-1 (Stauton et al., 1992, J. Exp. Med. 176: 1471-1476; Martin et al., 1993, J. Virol. 67: 3561-68; Roep et al., 1994, Lancet 343: 1590-93); ICAM-2 (Damle et al., 1992, J. Immunol. 148: 665-71); ICAM-3 (Holness et al., 1995, J. Biol. Chem. 270: 877-84); LFA-3 (Kanner et al., 1992, J. Immunol. 148: 23-29); L1 glycoprotein (Doherty et al., 1995, Neuron 14: 57-66); TNF-R1 (Ashkenazi et al., 1991, Proc. Natl. Acad. Sci. USA 88: 10535-539); Lesslauer et al., 1991, Eur. J. Immunol. 21: 2883-86; Peppel et al., 1991, J. Exp. Med. 174: 1483-1489); TNF-R2 (Zack et al., 1993, Proc. Natl. Acad. Sci. USA 90: 2335-39; Wooley et al., 1993, J. Immunol. 151: 6602-07); CD44 (Aruffo et al., 1990, Cell 61: 1303-1313); CD28 and B7 (Linsley et al., 1991, J. Exp. Med. 173: 721-730); CTLA-4 (Lisley et al., 1991, J. Exp. Med. 174: 561-569); CD22 (Stamenkovic et al., 1991, Cell 66: 1133-1144); NP receptors (Bennett et al., 1991, J. Biol. Chem. 266: 23060-23067); and IgE receptor α (Ridgway and Gorman, 1991, J. Cell. Biol. 115: 1448.).

Immunoadhesin design combines the binding region(s) of the "adhesion" polypeptide with the hinge and Fc regions of an immunoglobulin heavy chain. Ordinarily, when preparing the preS fusion proteins of the present invention, nucleic acid encoding the desired preS polypeptide is fused at the C-terminus of the desired sequence to the N-terminus of a nucleic acid sequence encoding an immunoglobulin constant domain sequence, however fusion to the N-terminus of the desired preS sequence is also possible. Typically, in such fusions the encoded fusion polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the preS immunoglobulin fusion protein.

A fusion protein comprising a desired preS region fused to an Fc region may have advantages over the free preS form. Such advantages include but are not limited to facilitation of purification (e.g., by binding to protein A) and increased stability of the fusion protein (i.e., both during expression, purification, and after injection or expression within the host animal).

Methods of producing fusion proteins include, for example, the following steps (the order of some steps may be interchanged): (a) identifying and cloning the correct gene segment encoding the desired preS region; (b) cloning the gene segments encoding the constant region or desired part thereof; (c) ligating the preS region to the constant region so that the complete fusion protein is encoded in a transcribable and translatable form; (d) ligating this construct into a vector containing a selectable marker and gene control regions such as promoters, enhancers and poly(A) addition signals; (e) introducing the DNA into eukaryotic cells (transfection) such as mammalian lymphocytes; and culturing the host cell under conditions suitable for expression of the fusion protein.

Using the sequence information provided herein, the nucleic acids may be synthesized according to a number of standard methods known in the art. Oligonucleotide synthesis, is carried out on commercially available solid phase oligonucleotide synthesis machines or manually synthesized using the solid phase phosphoramidite triester method described by Beaucage et. al., 1981 *Tetrahedron Letters.* 22: 1859-1862.

Once a nucleic acid encoding a preS polypeptide is synthesized, it may be amplified and/or cloned according to standard methods in order to produce recombinant polypeptides. Molecular cloning techniques to achieve these ends are known in the art. A wide variety of cloning and in vitro amplification methods suitable for the construction of recombinant nucleic acids are known to those skilled in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook et al., MOLECULAR CLONING: A LABORATORY MANUAL, volumes 1-3 (3$^{rd}$ ed., Cold Spring Harbor Press, NY 2001).

Once the nucleic acid for a preS polypeptide is cloned, a skilled artisan may express the recombinant gene(s) in a variety of engineered cells. Examples of such cells include bacteria, yeast, filamentous fungi, insect (especially employing baculoviral vectors), and mammalian cells. It is expected that those of skill in the art are knowledgeable in the numerous expression systems available for expressing the preS polypeptides of the invention.

The present invention also provides for analogs of polypeptides which comprise a preS sequence. Analogs may differ from naturally occurring proteins or polypeptides by conservative amino acid sequence differences or by modifications which do not affect sequence, or by both. For example, conservative amino acid changes may be made, which although they alter the primary sequence of the protein or polypeptide, do not normally alter its function (e.g., secretion and capable of blocking virus infection). Conservative amino acid substitutions typically include substitutions within the following groups: (a) glycine, alanine; (b) valine, isoleucine, leucine; (c) aspartic acid, glutamic acid; (d) asparagine, glutamine; (e) serine, threonine; (f) lysine, arginine; (g) phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

The present invention should also be construed to encompass "mutants," "derivatives," and "variants" of the peptides of the invention (or of the DNA encoding the same) which mutants, derivatives and variants are altered in one or more amino acids (or, when referring to the nucleotide sequence encoding the same, are altered in one or more base pairs) such that the resulting peptide (or DNA) is not identical to the sequences recited herein, but has the same biological property as the preS polypeptides disclosed herein, in that the peptide has biological/biochemical properties. A biological property of the polypeptides of the present invention should be construed but not be limited to include, the ability of the polypeptide to be secreted when expressed in a host cell and the ability of the protein to inhibit virus infection.

Further, the invention should be construed to include naturally occurring variants or recombinantly derived mutants of preS polypeptide sequences, which variants or mutants render the polypeptide encoded thereby either more, less, or just as biologically active as a polypeptide comprising at least the first 30 amino acids of preS1 of the invention.

The biological activity of the preS polypeptides of the invention, whether the polypeptide is considered an IA or not, is the ability of the polypeptides of the invention to inhibit infection of HBV and/or HDV of hepatocytes. In some aspects, the biological activity refers to both the ability of the preS polypeptides to be secreted from a host cell and capable of inhibiting HBV and/or HDV infection of hepatocytes.

Vectors

Nucleic acids encoding the desired preS polypeptide or equivalents may be replicated in wide variety of cloning vectors in a wide variety of host cells.

In brief summary, the expression of natural or synthetic nucleic acids encoding a preS polypeptide will typically be achieved by operably linking a nucleic acid encoding the preS polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In some aspects, the expression vector is selected from the group consisting of a viral vector, a bacterial vector, and a mammalian cell vector. Numerous expression vector systems exist that comprise at least a part or all of the compositions discussed above. Prokaryote- and/or eukaryote-vector based systems can be employed to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (e.g., WO 01/96584; WO 01/29058; and U.S. Pat. No. 6,326,193).

For expression of the preS polypeptides or portions thereof, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (e.g., U.S. Pat. No. 4,683,202, U.S. Pat. No. 5,928,906).

Naturally, it will be important to employ a promoter and/or enhancer that effectively directs the expression of the DNA segment in the cell type, organelle, and organism chosen for expression. The promoters employed may be constitutive, tissue-specific, inducible, and/or useful under the appropriate conditions to direct high level expression of the introduced DNA segment, such as is advantageous in the large-scale production of recombinant proteins and/or polypeptides. The promoter may be heterologous or endogenous.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a preS polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (e.g., Ui-Tei et al., 2000 *FEBS Letters* 479:

79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Method for Expression

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL, volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape.

Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 *Glycobiology* 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains (T E Creighton (1983) Proteins: Structure and Molecular Properties, W.H. Freeman & Co., San Francisco, pp. 79-86).

Regardless of the method used to introduce exogenous nucleic acids into a host cell or otherwise expose a cell to the nucleic acid, in order to confirm the presence of the recombinant DNA sequence in the host cell, a variety of assays may be performed. Such assays include, for example, "molecular biological" assays well known to those of skill in the art, such as Southern and Northern blotting, reverse transcription polymerase chain reaction (RT-PCR) and PCR; "biochemical" assays, such as detecting the presence or absence of a particular peptide, e.g., by immunological means (ELISAs and Western blots).

Following the generation of the preS polypeptide or portions thereof, the preS polypeptide or portions thereof can be used in a wide range of experimental and/or therapeutic purposes.

Therapy

The therapeutic applications of the invention relates to the discovery that the polypeptides of the invention were observed to be secreted from a host cell and capable of inhibiting virus infection of hepatocytes. For example, it was observed that a polypeptide comprising at least the first 30 amino acids of the preS1 region from HBV was effectively secreted from a host cell and was able to inhibit viral infection of hepatocytes. Other polypeptides observed to exhibit this biological activity (e.g., secretion from a host cell and inhibition of viral infection) include, but are not limited to a polypeptide comprising preS1 and preS2, an IA comprising the first 30 amino acid of preS1, and an IA comprising preS1 and preS2.

The polypeptides, polynucleotides, vectors and host cells of the present invention may be used in the prevention and/or treatment of HBV and/or HDV infections. Accordingly, the invention also provides a method of treating or preventing HBV and/or HDV infection in a human or animal which comprises administering to the human or animal in need thereof an effective amount of a preS polypeptide by way of a polypeptide, a polynucleotide, a vector, and/or a host cell of the invention. Regardless of how the desired preS polypeptide is provided to a human or animal, the preS polypeptide can be used to inhibit in vivo hepatocyte infection by HBV through preventing binding and/or internalization of HBV particles to hepatocytes.

In a further aspect, the present invention provides a vaccine composition comprising a polypeptide, a polynucleotide, a vector, a cell of the invention, or any combination thereof. The vaccine can be combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The preS polypeptide of the invention may be administered to the human or animal by direct injection. Preferably the preS polypeptide is combined with a pharmaceutically acceptable carrier or diluent to produce a pharmaceutical composition. Typically, each preS polypeptide is administered at a dose of from about 0.01 to 30 µg/kg body weight, preferably from about 0.1 to 10 µg/kg, more preferably from 0.1 to 1 µg/kg body weight.

The preS polypeptide of the invention may be administered directly as a naked nucleic acid construct, preferably further comprising flanking sequences homologous to the host cell genome. When the expression cassette is administered as a naked nucleic acid, the amount of nucleic acid administered is typically in the range of from 1 µg to 10 mg, preferably from 100 µg to 1 mg.

Typically dosages of the compound of the invention which may be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 milligram to about 10 grams per kilogram of body weight of the animal. More preferably, the dosage will vary from about 10 milligrams to about 1 gram per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Vaccines may be prepared from one or more preS polypeptide of the invention. The polypeptides of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgment of the practitioner.

Accordingly, the invention provides a therapeutical method for the prevention of and/or the treatment of HBV and/or HDV infection that comprises administration of the desired preS polypeptide (whether it be in the form of a polypeptide, a polynucleotide, a vector, or a cell) of the invention to a patient in need thereof.

B. Lentivirus Vectors Carrying Hepatitis B Virus Antigens

The present invention provides a recombinant lentivirus capable of infecting non-dividing cells as well as methods and means for making same. The virus is useful for the in vivo and ex vivo transfer and expression of nucleic acid sequences.

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

The invention provides a method of producing a recombinant lentivirus capable of infecting a non-dividing cell comprising transfecting a suitable host cell with a vector carrying the packaging functions, namely gag, pol and the S gene derived from HBV that encodes L, M, and S HBV envelope proteins. In some aspects, the host cell is transfected with two or more vectors carrying the packing functions. For example, a first vector can provide a nucleic acid encoding a viral gag and a viral pol and another vector can provide a nucleic acid encoding a viral envelope proteins (e.g., HBV envelope proteins) to produce a packaging cell. Introducing a vector providing a heterologous gene, herein identified as a transfer vector, into that packaging cell yields a producer cell which releases infectious viral particles carrying the foreign gene of interest.

Accordingly, the present invention relates to compositions and derivatives thereof that are useful for constructing a lentivirus pseudovirus bearing HBV surface proteins (e.g. L, M and/or S). The invention is partly based on the discovery that HBV surface proteins can be expressed on the surface of a lentivirus, thereby allowing the lentiviral vector to specifically target hepatocytes for infection. As such, the invention also includes viral-based therapies able to target delivery of therapeutic agents or compounds to hepatocytes or otherwise cells associated with liver disease.

In certain instances, the HBV lentivirus pseudovirus bearing HBV surface proteins can be used to target hepatocytes infected with HCV. Without wishing to be bound by any particular theory, it is believed that HBV and HCV use different hepatocytes receptors. Therefore, the invention provides a method for treating a mammal infected with HCV by way of an HBV lentivirus pseudovirus bearing HBV surface protein to provide a type of targeted gene therapy.

Preparation of Pseudovirus

The present invention encompasses a composition comprising a lentiviral-HBV pseudovirus. By way of example, a pseudovirus expressing HBV surface antigens is constructed by transfecting a host cell with one or more plasmids comprising a nucleotide sequence encoding a necessary component of the pseudovirus. Generally the vectors are plasmid-based or virus-based, and are configured to carry the essential sequences for incorporating foreign nucleic acid, for selection (e.g., selection marker) and for transfer of the nucleic acid into a host cell.

Accordingly, the invention includes generating a pseudovirus in several ways. In one embodiment, host cells are transfected with multiple plasmids. The first plasmid comprises a nucleotide sequence encoding a modified lentiviral genome. The modified genome is replication-defective.

The invention further includes a second plasmid comprising nucleotide sequences that encode a HBV surface protein or otherwise an envelope protein. The envelope protein(s) allows transduction of cells of human and other species. The plasmid can also comprise a nucleotide sequence encoding the L surface protein of HBV, the M surface protein of HBV, the S surface protein of HBV, or any combinations thereof.

The vector providing the nucleic acid sequence encoding viral envelope proteins is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter, etc. In some cases, the promoter-enhancer elements are located within or adjacent to the LTR sequences.

In another embodiment, the invention includes generating a pseudovirus by transfecting host cells with a single vector. Accordingly, the invention includes a plasmid comprising a nucleotide sequence encoding a modified lentivirus and an in-frame HBV surface protein. For example, the plasmid can comprise a nucleotide sequence encoding a modified lentivirus and an HBV surface protein under transcriptional control of a single promoter. Alternatively, the plasmid can comprise a nucleotide sequence encoding a modified lentivirus and an HBV surface protein under transcriptional control of separate promoters.

Using the information provided herein, the HBV surface proteins can be produced recombinantly using standard techniques well known to those of skill in the art or produced by a host cell in vivo. For example, the sequences of HBV set forth in Genebank AAK58874.1 can be used to engineer the desired pseudovirus. The nucleic acid sequence may be optimized to reflect particular codon "preferences" for various expression systems according to methods known in the art.

Reporter Genes and Tags

In order to assess the expression of a HBV surface proteins or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells.

Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (e.g., Ui-Tei et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Cloning

Using the sequence information provided herein, the nucleic acids may be synthesized according to a number of standard methods known in the art. Oligonucleotide synthesis, is carried out on commercially available solid phase oligonucleotide synthesis machines or manually synthesized using the solid phase phosphoramidite triester method described by Beaucage et. al., 1981 *Tetrahedron Letters*. 22: 1859-1862.

Once a nucleic acid encoding a HBV surface protein is synthesized, it may be amplified and/or cloned according to standard methods in order to produce recombinant polypeptides. Molecular cloning techniques to achieve these ends are known in the art. A wide variety of cloning and in vitro amplification methods suitable for the construction of recombinant nucleic acids are known to those skilled in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook et al., MOLECULAR CLONING: A LABORATORY MANUAL, volumes 1-3 ($3^{rd}$ ed., Cold Spring Harbor Press, NY 2001).

Once the nucleic acid for a HBV surface protein is cloned, a skilled artisan may express the recombinant gene(s) in a variety of engineered cells. Examples of such cells include bacteria, yeast, filamentous fungi, insect (especially employing baculoviral vectors), and mammalian cells. It is expected that those of skill in the art are knowledgeable in the numerous expression systems available for expressing the HBV envelop proteins of the invention.

The present invention also provides for analogs of polypeptides which comprise a HBV surface protein sequence. Analogs may differ from naturally occurring proteins or polypeptides by conservative amino acid sequence differences or by modifications which do not affect sequence, or by both. Conservative amino acid changes and modifications are described in Part A above.

This aspect of the present invention should also be construed to encompass "mutants," "derivatives," and "variants" of the HBV surface proteins of the invention (or of the DNA encoding the same) which mutants, derivatives and variants are altered in one or more amino acids (or, when referring to the nucleotide sequence encoding the same, are altered in one or more base pairs) such that the resulting peptide (or DNA) is not identical to the sequences recited herein, but has the same biological property as the HBV surface proteins disclosed herein, in that the proteins have biological/biochemical properties. A biological property of the polypeptides of the present invention should be construed but not be limited to include, the ability of the HBV surface proteins to bind to hepatocytes and mediate incorporation of viral genome into said hepatocyte.

Further, the invention should be construed to include naturally occurring variants or recombinantly derived mutants of HBV surface proteins sequences, which variants or mutants render the polypeptide encoded thereby either more, less, or just as biologically active as wild type HBV surface proteins.

The biological activity of the pseudovirus of the invention is the ability of the lentiviral HBV pseudovirus to infect human hepatocytes, either in vivo or in vitro. In some aspects, the biological activity refers to both the ability of the HBV surface proteins to be incorporated into the HIV surface as well as infection of hepatocytes. In other aspects, the biological activity refers to the ability of the lentivirus HBV pseudovirus to deliver therapeutic agents to hepatocytes.

Vectors

Nucleic acids encoding the desired HBV surface proteins or equivalents may be replicated in wide variety of cloning vectors in a wide variety of host cells.

In brief summary, the expression of natural or synthetic nucleic acids encoding HBV surface proteins will typically be achieved by operably linking a nucleic acid encoding the HBV surface proteins or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In some aspects, the expression vector is selected from the group consisting of a viral vector, a bacterial vector, and a mammalian cell vector. Numerous expression vector systems exist that comprise at least a part or all of the compositions discussed above. Prokaryote- and/or eukaryote-vector based systems can be employed to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (e.g., U.S. Pat. No. 4,683,202, U.S. Pat. No. 5,928,906).

Naturally, it will be important to employ a promoter and/or enhancer that effectively directs the expression of the DNA segment in the cell type, organelle, and organism chosen for expression. The promoters employed may be constitutive, tissue-specific, inducible, and/or useful under the appropriate conditions to direct high level expression of the introduced DNA segment, such as is advantageous in the large-scale production of recombinant proteins and/or polypeptides. The promoter may be heterologous or endogenous.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Method for Expression

The present invention also encompasses a cell type appropriate for transfection with the above plasmids. Recipient cells capable of expressing the gene products are transfected with the genes. The transfected recipient cells are cultured under conditions that permit expression of the incorporated genes such that when plasmid(s) encoding HBV surface proteins are overexpressed in conjunction with the modified HIV-1 genome, with or without a reporter gene, they are co-assembled on the cell surface, essentially packaging HBV surface proteins into HIV particles, creating a lentiviral HBV pseudovirus. Infectious pseudotype virus is harvested directly from the culture medium.

Any cell or cell line that can be transduced with a lentiviral vector particle can be used in the invention. Examples of such cells include, but are not limited to: Jurkat cells (a human T cell line), H9 cells (human T-lymphoid cell line), A3.01 cells (human T-lymphoid cell line), C8166 cells (human T-lymphoid cell line), COS-7 cells (an African green monkey fibroblast cell line), human peripheral blood lymphocytes (PBLs), monkey PBLs, feline PBLs, a feline CD4+ T cell line, 293 cells (a human kidney fibroblast cell line), 293T cells (a human kidney fibroblast cell line), mammalian peripheral blood dendritic cells, mammalian hepatocytes, human mast cell progenitors, mammalian macrophages, mammalian follicular dendritic cells, mammalian epidermal Langerhans cells, mammalian megakaryocytes, mammalian microglia, mammalian astrocytes, mammalian oligodendroglia, mammalian CD8+ cells, mammalian retinal cells, mammalian renal epithelial cells, mammalian cervical cells, mammalian rectal mucosa cells, mammalian trophoblastic cells, mammalian cardiac myocytes, human neuroblastoma cells, mammalian CD4+ cells, mammalian hematopoietic stem cells, mammalian glial cells, adult mammalian neural stem cells, mammalian neurons, mammalian lymphocytes, and mammalian fibroblasts. Lists of CD4+ and CD4− cell types which are infectable by HIV have been compiled (see, Rosenburg and Fauci, 1989, Adv. Immunol. 47:377-431; and Connor and Ho, 1992, in AIDS: etiology, diagnosis, treatment, and prevention, 3rd edition, Hellman and Rosenburg (eds) Lippincott, Philadelphia. Also see Vigna and Naldini, 2000, J. Gene Med. 5:308-316).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., Molecular Cloning: A Laboratory Manual, volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized for the expression of HBV surface proteins, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 *Glycobiology* 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains (T E Creighton (1983) Proteins: Structure and Molecular Properties, W.H. Freeman & Co., San Francisco, pp. 79-86).

Regardless of the method used to introduce exogenous nucleic acids into a host cell or otherwise expose a cell to the nucleic acid, in order to confirm the presence of the recombinant DNA sequence in the host cell, a variety of assays may be performed. Such assays include, for example, "molecular biological" assays well known to those of skill in the art, such as Southern and Northern blotting, reverse transcription polymerase chain reaction (RT-PCR) and PCR; "biochemical" assays, such as detecting the presence or absence of a particular peptide, e.g., by immunological means (ELISAs and Western blots).

Following the generation of the lentivirus HBV pseudotype virus, lentivirus HBV pseudotype can be used in a wide range of experimental and/or therapeutic purposes.

Therapy

The therapeutic applications of the invention relates to the discovery that the lentivirus HBV pseudovirus of the invention infect primary human hepatocytes. Accordingly, the invention encompasses the use of a lentivirus HBV pseudovirus for hepatocyte targeted therapy.

The polypeptides, polynucleotides, vectors and host cells of the present invention may be used in the prevention and/or treatment of any disease requiring targeting of hepatocytes. Accordingly, the invention encompasses gene therapy using a lentivirus-HBV pseudovirus to target hepatocytes.

The present invention envisions treating a liver disease, for example liver cancer or hepatitis and the like, by the administration of a foreign gene to a mammal in need thereof. In certain aspects, the lentivirus HBV pseudovirus can be used to target HCV infected cells because HBV and HCV use different hepatocyte receptors. In any event, a foreign gene can be any nucleic acid of interest which can be transcribed. Generally the foreign gene encodes a polypeptide. Preferably the polypeptide has some therapeutic benefit. The polypeptide may supplement deficient or nonexistent expression of an endogenous protein in a host cell. The polypeptide can confer new properties on the host cell, such as a chimeric signaling receptor. The artisan can determine the appropriateness of a foreign gene practicing techniques taught herein and known in the art.

The present invention also includes gene constructs which comprise nucleotide sequences that encode heterologous proteins which, when introduced into hepatocytes, introduce a gene whose expression has a therapeutic effect in the individual. The cells of the present invention can be genetically modified by having exogenous genetic material introduced into the cells, to replace a missing gene product, e.g. UGT1A1, LDL receptor, coagulation factors, or repair genes associated with inherited metabolic, functional or structural disorders such as Crigler-Najjar syndrome-1, familial hypercholesterolemia, tyrosinemia, mucopolysaccaridoses, urea cycle disorders, hemophilia, etc. In addition, by having the cells genetically modified to produce such a molecule, the cell can provide an additional therapeutic effect to the patient when transplanted into a patient in need thereof.

Tyrosinemia is a genetic disorder characterized by elevated blood levels of the amino acid tyrosine. Tyrosinemia is caused by the shortage of one of the enzymes required for the multistep process that breaks down tyrosine. Type I tyrosinemia is the most severe form of this disorder and is caused by a shortage of the enzyme fumarylacetoacetate hydrolase. Symptoms usually appear in the first few months of life and include failure to gain weight and grow at the expected rate (failure to thrive), diarrhea, vomiting, yellowing of the skin and whites of the eyes (jaundice), cabbagelike odor, and increased tendency to bleed (particularly nosebleeds). Type I tyrosinemia can lead to liver and kidney failure, problems affecting the nervous system, and an increased risk of liver cancer.

Mutations in the FAH, HPD, and TAT genes cause tyrosinemia. In the liver, tyrosine is broken down in a five-step process to harmless molecules that are either excreted by the kidneys or used in reactions that produce energy. Mutations in the fumarylacetoacetate hydrolase (FAH), 4-hydroxyphenylpyruvate dioxygenase (HPD), or tyrosine aminotransferase (TAT) gene cause a shortage of one of the enzymes in this multistep process. The resulting enzyme deficiency leads to a toxic accumulation of tyrosine and its byproducts, which can damage the liver, kidneys, nervous system, or other tissues.

In addition to providing a desired gene to hepatocytes, the invention encompasses the use of a vector encoding HBV envelope proteins to target hepatocytes and have the hepatocytes express the envelope protens of HBV. This would lead to the release of non-infectious sub-viral particles and subsequently provide a direct protective effect against HBV infection.

Alternatively the therapeutic agent can be an inhibitor of an undesirable gene. That is, it may be desirable to suppress the expression of a gene when it is over-expressed. Where a cell proliferative disorder is associated with the expression of a gene, nucleic acid sequences that interfere with the expression of a gene at the translational level can be used. The approach can utilize, for example, antisense nucleic acid, ribozymes or triplex agents to block transcription or translation of a specific mRNA, either by masking that mRNA with an antisense nucleic acid or triplex agent, or by cleaving same with a ribozyme. Si-RNA is also a desirable means for suppressing expression of a gene.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful can be designed by incorporating target sequences into the basic ribozyme structure which are complementary to the mRNA sequence of the desired target gene. Ribozymes targeting the desired gene may be synthesized using commercially available reagents (Applied Biosystems, Inc., Foster City, Calif.) or they may be genetically expressed from DNA encoding them.

A small interfering RNA (siRNA) is an RNA molecule comprising a set of nucleotides that is targeted to a gene or polynucleotide of interest. As used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein.

The invention includes lentiviral vectors encoding a gene that can be used to inhibit viral replication in cells. For example, lentiviral siRNA vectors targeting multiple highly conserved regions in the HBV genome can inhibit HBV replication of all strains of the virus. Other genes, however, may be targeted for modulation (e.g., suppression or silencing) using lentiviral siRNA vectors. Genes to be targeted using lentiviral siRNA vectors include, without limitation, those whose expression is correlated with an undesired phenotypic trait. Thus, genes relating to hepatits, liver cancer, and other liver related diseases might be targeted. Cancer-related genes include oncogenes (e.g., K-ras, c-myc, bcr/abl, c-myb, c-fms, c-fos and cerb-B), tumor suppressor genes (e.g., bcl-2 and bcl-X1) and metastatic genes. Viral genes include hepatitis B and C. Numerous other genes relating to these diseases or others can also be targeted.

Accordingly, the invention features a lentiviral vector (e.g., a self-inactivating vector) that includes a nucleotide sequence encoding a small interference RNA. The lentiviral vector can be one included within a lentiviral virion. The small interference RNA can be on specific for a gene associated with cancer such as Sca-2 or it can be specific for a gene present in a virus (e.g., HIV) such as gag, pol, int, or vpu from HIV-1.

In another aspect of the invention, proteins associated with liver disease can be inhibited by way of inactivating and/or sequestering the protein. As such, inhibiting the effects of such a protein can be accomplished by using a transdominant negative mutant. Alternatively an intracellular antibody specific for the desired protein, otherwise known as an antagonist to the protein may be used.

One skilled in the art recognizes that different methods of delivery may be utilized to administer a nucleotide sequence comprising a therapeutic agent or vector into a cell. Examples include: (1) methods utilizing physical means, such as electroporation (electricity), a gene gun (physical force) or applying large volumes of a liquid (pressure); (2) methods wherein said vector is complexed to another entity, such as a liposome, aggregated protein or transporter molecule; and (3) methods wherein said nucleotide sequence is packaged into a viral genome.

The invention encompasses administration of the compositions of the present invention to elicit over time a protective immune response. Thus, the invention allows for a single injection of such an HBV lentivirus to possibly confer resistance to HBV and/or HDV infection for a lifetime. Such protection conferred by a single injection would be superior to all current HBV vaccination which requires at least three injections.

Administration of the compositions of the present invention may be accomplished through the administration of the nucleic acid molecule (see, for example, Feigner et al., U.S. Pat. No. 5,580,859, Pardoll et al. 1995; Stevenson et al. 1995; Moiling 1997; Donnelly et al. 1995; Yang et al. II; Abdallah et al. 1995). Pharmaceutical formulations, dosages and routes of administration for nucleic acids are generally disclosed, for example, in Feigner et al., supra.

Furthermore, the actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Compositions containing the therapeutic agent may also contain a suicide gene i.e., a gene which encodes a product that can be used to destroy the cell. In many gene therapy situations, it is desirable to be able to express a gene for therapeutic purposes in a host cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk:: Tmk) and AZT; and deoxycytidine kinase and cytosine arabinoside.

Transfer of an exogenous nucleic acid into a host cell or organism by a lentiviral vector can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods. For instance, mRNA produced from an exogenous nucleic acid can be detected and quantified using a Northern blot and reverse transcription PCR (RT-PCR).

Expression of an RNA from the exogenous nucleic acid can also be detected by measuring an enzymatic activity or a reporter protein activity. For example, activity of the exogenous nucleic acid can be measured indirectly as a modulation in target nucleic acid expression as an indication that the exogenous nucleic acid is producing the effector RNA.

The present invention also includes plasmids therapeutic compounds covalently linked to, or packaged within the lentiviral pseudovirus that may have beneficial effects when delivered directly to hepatocytes. Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a pre-selected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly(lactic acid) or ethylenevinylacetate copolymers. In addition to being incorporated, these agents can also be used to trap the compound in microcapsules.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Compositions Containing HBV Pre-S Domains

The experiments disclosed herein were conducted to explore at least the roles of the preS1 and/or preS2 sequences of HBV. The results disclosed herein demonstrate that as few as 30 amino acids from the N terminus of preS1 can promote protein secretion. In addition, the compositions discussed in these examples were observed to inhibit infection of primary human hepatocytes by HBV and/or HDV.

The materials and methods employed in the experiments disclosed herein are now described.

Cells and Viruses

Human embryonic kidney 293T and T-REx cells, and human hepatoblastoma Huh7 cells, were grown in Dulbecco's modified Eagle's media supplemented with 10% fetal calf serum. Primary human hepatocytes in 48-well configuration plated as confluent monolayers on rat-tail collagen were obtained commercially (Admet, Cambrex, or CellzDirect) and maintained in Hepatostim medium supplemented with 0.01 mg/ml epidermal growth factor, receptor grade, both from BD Biosciences. All cells were maintained at 37° C. in 5% $CO_2$. HDV and HBV were assembled in vitro from transfected Huh7 cells.

Immunoadhesin (IA) Construction and Expression

Unless otherwise stated, the HBV sequences used in this example were for serotype adw2, genotype A (genbank AAK58874.1). Vector constructions were as in Chai and Bates (Chai, et al., 2006, Proc. Natl. Acad. Sci., USA 103: 5531-5536). Briefly, various PreS regions were amplified using specific primers and PCR. These were inserted into plasmid pCAGGS-rlg. Additional point mutations were created using a QuickChange® kit (Stratagene). Constructs were transfected into 293T cells using calcium phosphate or into Huh7 cells using Lipofectamine™ 2000 (Invitrogen). The media were supplemented with 10% fetal calf serum that had been depleted of immunoglobulin G (Invitrogen). After 2 days, the media were harvested and clarified, while the cells were washed with phosphate buffered saline (PBS) and then lysed in 50 mM Tris (pH 8.0), 5 mM EDTA, 150 mM NaCl, 1% Triton X-100, and protease inhibitor cocktail (Roche). T-REx 293 cell lines (Invitrogen) conditionally expressing IA were created using procedures previously described (Chang, et al., 2005, J. Virol., 79:8182-8188).

Immunoblot Procedures

Figure 2:
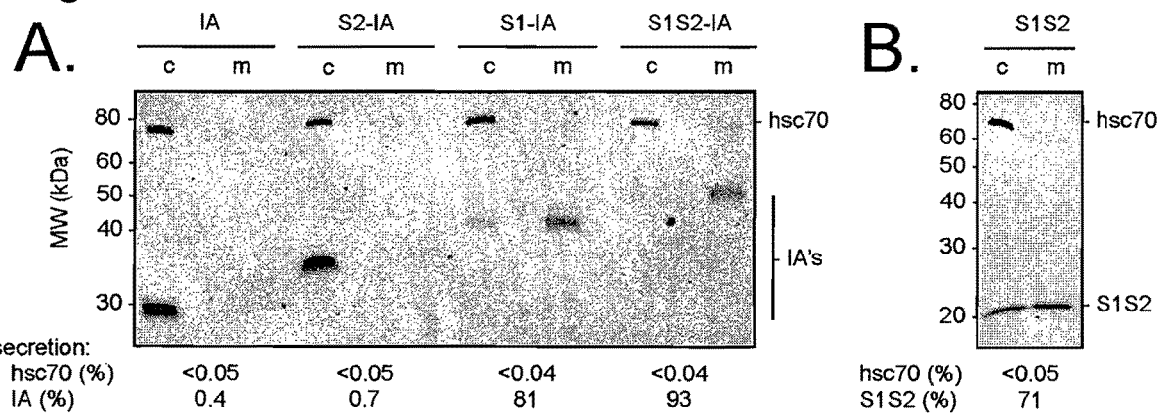

Samples were boiled in Laemmli buffer, with or without DTT, prior to analysis on 12% pre-cast Duramide gels (Cambrex). After electrophoresis and transfer to nitrocellulose membranes, IA were detected using infra-red dye-labeled goat anti-rabbit antibody (LI-COR). The hsc70 was detected on the same membrane using a primary mouse monoclonal antibody (Affinity Bioreagents) followed by a goat anti-mouse antibody labeled with a different infra-red dye (LI-COR). Molecules containing the HBV preS2 domain were detected using as primary antibody S-26, a mouse monoclonal as described in Sominskaya, et al., 1992, Immunol. Letters, 33:169-172. Similarly, molecules containing preS1 were detected using Ma18/7, another mouse monoclonal as described in Heermann, et al., 1987, Intervirology, 28:14-25. Detection and quantitation were achieved using a two-color infra-red laser scanning apparatus and associated software (Odyssey, LI-COR). This system has the advantage of a linear response over a >4,000-fold range. To determine the molar concentration of secreted preS for each of the IA fusion proteins the immunoblat data as in FIG. 2A, were normalized relative to known amounts of a protein-A affinity-purified IA (Chai, et al., 2006, Proc. Natl. Acad. Sci., USA 103:5531-5536). Such data were then used to normalize the amounts of the non-fusion protein S1S2, using immunoblot data as in FIG. 2B.

Radioactive Labeling of IA

After transient transfection, cells were washed and then incubated with media containing 3H myristic acid (10 μCi/ml, New England Nuclear). After 2 days, the media and cells were harvested as described above. IA were selected by binding to protein-A agarose (Invitrogen) and then subjected to electrophoresis and electrotransfer to a nitrocellulose membrane. The $^3$H on the dried membrane was detected and quantitated with a special screen and bio-imager (Fujifilm BAS-2400). Then the membrane was subjected to immunoblot to detect IA, as described elsewhere herein.

Biological Activity

In order to test inhibitory activity of the IA and related proteins, primary human hepatocytes infected in the presence of 5% polyethylene glycol 8000 (Sigma) were used with in vitro assembled HDV at a multiplicity of 10 genome equivalents (GE) per cell, or by HBV at a multiplicity of 50 GE/cell. In some instances, the IA and related proteins were observed to be present during the 16 hour infection period. One related protein was the S1S2, lacking the Fc domain (FIG. 1B). Another was a synthetic peptide corresponding to positions 2-48 of the ayw PreS1, with myristoylation at the N terminal glycine as described in Engelke, et al., 2006, Hepatology, 43:750-760. After 7-8 days total, cell RNA was extracted and HDV antigenomic RNA and HBV RNA were quantitated using real-time PCR.

The results of the experiments presented in this Example are now described.

Design, Transient Expression, and Secretion of IA with HBV preS Sequences

The result presented in this example involves the expression of various polypeptide as diagramed in FIG. 1B. These are fusions of HBV preS sequences to the Fc region of a rabbit IgG. Two days after transient transfection into 293T, a line of human embryonic kidney cells, aliquots of the total cell proteins and the tissue culture media were examined by immunoblot for the presence of IA, using dye labeled goat anti-rabbit antibody. The results, with quantitation, are shown in FIG. 2A. All of the polypeptides and fusion proteins were expressed in transfected cells. However, they differed in terms of secretion. It was observed that the IA without HBV sequences was not secreted, consistent with the lack of a signal peptide. It was also observed that the S2-IA was not secreted. Without wishing to be bound by any particular theory, it is believed that these results support the reported interpretation that preS2 does not contain a signal activity (Eble, et al., 1990, J. Virol., 64:1414-1419). S1-IA and S1S2-IA were efficiently secreted, with >80% of the total IA being present in the medium. (It should be understood that the % secretion as measured here is really the steady-state distribution of the protein in the media relative to the sum of the accumulations in the cells and media.)

These results presented herein support the interpretation that preS1 contains significant secretion-directing activity and that the presence of preS2 has no negative effect on this ability. While these experiments were performed in 293T cells, comparable results for expression and secretion of IA in Huh7, a human hepatoblastoma cell line were observed.

It should be noted that with S1-IA and S1S2-IA, the concentration accumulated in the media during just 2 days was determined to be as high as 1800 nM (about 80 µg/ml). Without wishing to be bound by any particular theory, it can be deduced that in this period the average cell expressed 700 million IA molecules, and this is a lower estimate that does not allow for the efficiency of DNA transfection or for post-translational protein turnover.

As an internal negative control for secretion, each sample was assayed for hsc70, an abundant host protein that is also known to interact with a domain of HBV preS1 in the cytosol (Loffler-Mary, et al., 1997, Virology, 235:144-152). No hsc70 was detected in the media (FIG. 2A). An additional control, beta-actin was not observed to be released into the media. Thus, it is believed that the integrity of the transfected cells was not compromised by either the transfection or the abundant expression and secretion of the IA.

In addition, experiments were designed to tested whether the released IA was actually a soluble protein. Media samples containing albumin and secreted S1S1-IA were clarified by low speed centrifugation and then subjected to ultracentrifugation, using conditions that pellet HDV and HBV subviral particles. It was observed that about >85% of the albumin and S1S2-IA remained in the supernatant. Without wishing to be bound by any particular theory, it is believed that because the IAs behaved similar to albumin, than IAs were soluble proteins.

The above studies indicated that preS1+preS2 or just preS1 was sufficient to direct IA secretion. This was an unexpected result since others observed that the preS sequences of HBV L were unable to direct the translocation of a fusion protein with globin into ER derived microsomes and thus concluded that no signal sequence was present in preS (Ostapchuk, et al., 1994, EMBO J., 13:1048-1057).

Secretion in the Absence of the Fc Domain

Without wishing to be bound by any particular theory, even though the Fc domain alone was not secreted (FIG. 2A), it may have contained a cryptic secretion signal that was activated by the fusion of preS sequences. Therefore, the following experiments were designed to test the expression and secretion of preS1 polypeptides in the absence of the Fc domain. A 174 amino acid protein, S1S2, was detected using a mouse monoclonal antibody specific for an epitope in preS2. The results, with quantitation, are shown in FIG. 2B. More than 70% of this protein was secreted into the medium. The preS1 domain in the absence of IA was also expressed and secreted. Since the 174 amino acids of S1S2 were sufficient for secretion, this excludes the possibility that secretion of IA species might be via a cryptic signal within the Fc domain.

Minimal Sequences Needed for IA Secretion

The following experiments were designed to determine the minimal sequences necessary for secretion. A series of truncations of preS1 sequences were tested. IA fusions made it possible to readily separate and quantitate the expression and secretion of IA fused to altered preS sequences. As summarized in Table 1, truncations of preS1 down to the 30 N terminal amino acids still gave efficient secretion (75%). Ten N terminal amino acids also gave secretion but were much less efficient (4%). Thus, it was concluded that the first 30 amino acids were sufficient for efficient secretion. As a control for this interpretation, an IA fusion was engineered to contain an N terminal methionine and amino acids from position 31 to the C terminus of preS2. This protein was expressed but not secreted (Table 1). Thus, it was concluded that the first 30 amino acids are both necessary and sufficient for secretion. These results were extended from 293T cells to Huh7 cells with comparable results.

In the above studies the HBV envelope sequences used were those of the adw2 serotype. Another commonly studied serotype is ayw. In terms of the preS1 domain, ayw differs in that it is 11 amino acids shorter at the N terminus. Moreover, in the next 48 amino acids that have homology to the adw2, there are 10 amino acid changes. Nevertheless, when these 48 amino acids from the preS1 domain of ayw were expressed as an IA, efficient secretion was observed (79%). The above mentioned differences in the N terminal preS1 sequence did not interfere with secretion.

TABLE 1

Effect of alterations in the preS domains on the efficiency of IA secretion

| | preS sequence expressed as IA | Secretion (%) |
|---|---|---|
| Trimmed domains: | | |
| 1-59 (SEQ ID NO: 1) | MGGWSSKPRKGMGTNLSVPNPLGFFPDHQLDPAFGANSNNP DWDFNPIKDHWPAANQVG | 68 |
| 1-30 (SEQ ID NO: 2) | MGGWSSKPRKGMGTNLSVPNPLGFFPDHQL | 75 |
| 1-10 (SEQ ID NO: 3) | MGGWSSKPRK | 4 |
| 1, 31-174 (SEQ ID NO: 4) | MDPAFGANSNNPDWDFNPIKDHWPAANQVG . . . PVTN | 0.3 |

TABLE 1-continued

Effect of alterations in the preS domains on the efficiency of IA secretion

| preS sequence expressed as IA | | Secretion (%) |
|---|---|---|
| Mutated 1-119 domain of S1-IA: | | |
| G2A, G13A (SEQ ID NO: 5) | M<u>A</u>GWSSKPRKGM<u>A</u>TNLSVPNPLGFFPDHQLD . . . HPQA | 71 |
| N15Q (SEQ ID NO: 6) | MGGWSSKPRKGMGT<u>Q</u>LSVPNPLGFFPDHQLD . . . HPQA | 64 |

The sequences are those of serotype adw2 (accession AAK58874.1) (SEQ ID NO: 7).
The amino acid replacements are underlined.
Immunoblot quantitation was as in FIG. 2A. Data are expressed as percentage of IA detected in medium relative to total in medium and cells.

Post-Translational Modifications of IA

During HBV replication the glycine penultimate to the N terminus of preS1 undergoes myristoylation (Persing, et al., 1987, J. Virol., 61:1672-1677). This modification is needed for HBV infectivity but not for assembly (Gripon, et al., 1995, Virology, 213:292-299). Mutation of this penultimate glycine, as well as the next glycine, at position 13 did not interfere with secretion of S1-IA (Table 1). Similar results were observed for S1S2-IA. This second glycine was assessed because it follows a methionine that is believed theoretically to be a secondary site for the initiation of translation.

Figure 3A:
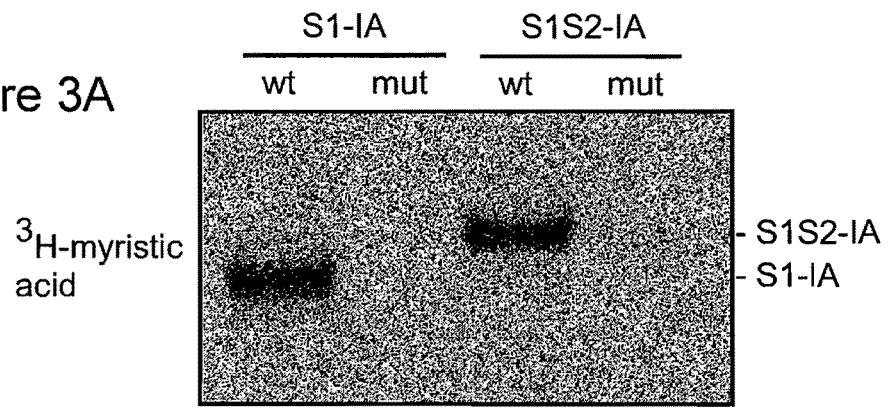
Figure 3B:
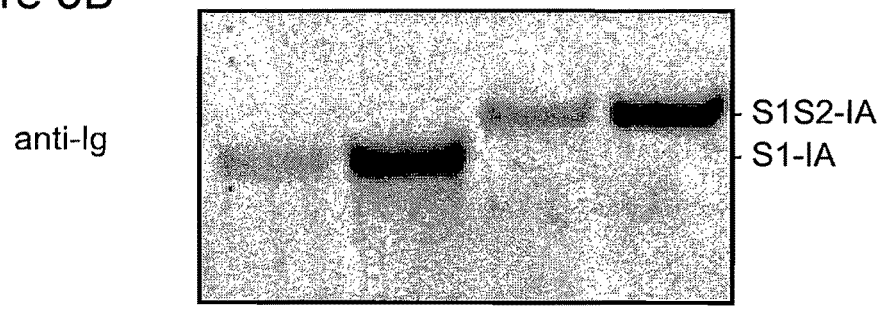
Figure 3C:

Furthermore, to confirm that myristoylation was occurring on the wild type (wt) IA but blocked on the mutated forms, both proteins were tested for their ability to be labeled with $^3$H myristic acid. As shown in FIG. 3A, only the wt forms of S1-IA and S1S2-IA were labeled. The same membrane was used to perform immunoblots with detection via the Fc domain (FIG. 3B) and preS1 region (FIG. 3C). These results confirmed that the mutant proteins were efficiently expressed but not myristoylated. In addition, the extent of secretion of the myristoylated protein detected by $^3$H was not less than that of the total IA detected by immunoblot. It was observed that the $^3$H-labeled forms of S1-IA, S1S2-IA were secreted into the media. Also, it was observed that the 1-59 amino acid truncation of S1-IA (Table 1) was both myristoylated and secreted.

A second possible post-translational modification of the 30 amino acids was glycosylation. Specifically, previous studies have reported a cryptic N-glycosylation site at position 15 (Bruss, et al., 1995, J. Virol., 69:6652-6657). Mutation of this asparagine to glutamine on S1-IA did not have an observable effect on secretion (Table 1). Similar results were obtained for S1S2-IA. Without wishing to be bound by any particular theory, it is believed that glycosylation does not occur within the preS domain.

Immunoadhesins are able to form dimers through disulfide linkages in the immunoglobulin domain (Chamow, et al., 1996, Trends Biotechnol., 14:52-60). Experiments were designed to assess the effects of dimer formation on secretion of the immunoadhesin. It was observed that by electrophoresis under non-reducing conditions, the secreted S1-IA and S1S2-IA existed as dimmers at a 14% occurrence. Thus, based on these observations, it is believed that dimer formation was not essential for secretion to occur.

Certain IA can Inhibit Infection by HDV and HBV

Others have shown that peptides based on the N terminus of HBV preS1 are able to interfere with infection of primary hepatocytes and of HepaRG cells, a cell line made from a differentiated liver tumor (Gripon, et al., 2005, J. Virol., 79:1613-1622, Gripon, et al., 2002, Proc. Natl. Acad. Sci., USA 99:15655-15660). Furthermore, it is known that such inhibition ability is potently enhanced by the presence of the N terminal myristoylation (Gripon, et al., 2005, J. Virol., 79:1613-1622). Secreted IAs were tested for their ability to interfere with the infection of primary human hepatocytes by HDV. For these studies the source of IA was simple dilutions of the media from transiently transfected cells that both expressed and secreted the IA. To assess HDV replication the total RNA was extracted after 7 days and antigenomic RNA was quantitated by real-time PCR. A major advantage of measuring antigenomic rather than genomic RNA is that it eliminates what might be a residual signal of viral (genomic) RNA that somehow binds to the monolayer culture but does not undergo genome replication.

Figure 4:
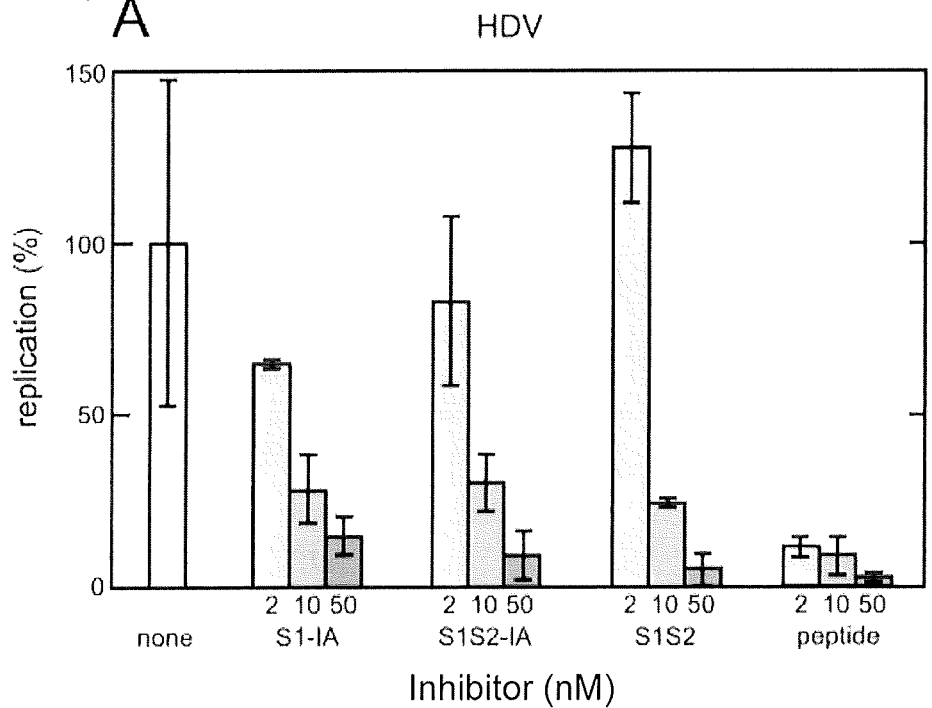
Figure 4:
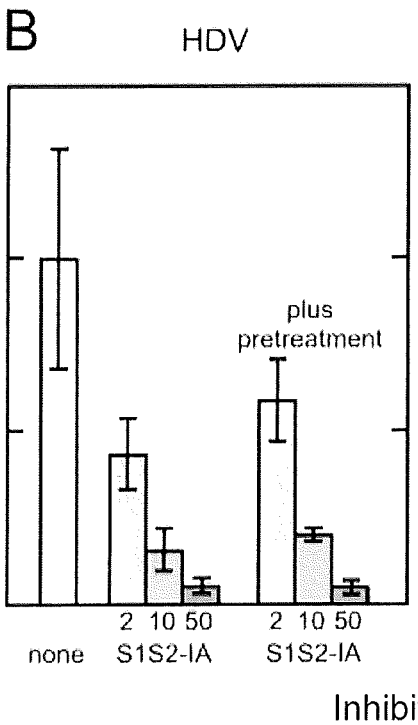
Figure 4:
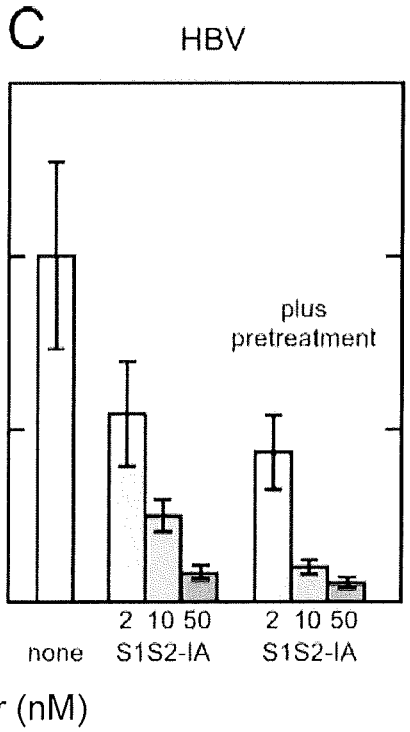

FIG. 4 summarizes the result. Briefly, at 50 nM final concentration, S1-IA and S1S2-IA both inhibited HDV replication by 90%. The S1S2 peptide, without the IA domain, was even more potent in inhibiting HDV replication (FIG. 4). However, neither the IA with only 59 amino acids from the N terminus of preS1, nor the mutated S1-IA that was not myristoylated, were able to inhibit HDV replication significantly, that is, less than a 2-fold effect.

Engelke et al. (Engelke, et al., 2006, Hepatology, 43:750-760) have reported that short acylated GST fusion proteins with amino acids 2-28 of an HBV preS1 could inhibit infection of primary human hepatocytes and HepaRG cells by HBV and HDV. Previously, Grpon et al. reported the use of acylated synthetic peptides to inhibit HBV infection (Gripon, et al., 2002, Proc. Natl. Acad. Sci., USA 99:15655-15660). As shown in FIG. 4, the inhibition of HDV replication by one such acylated peptide was compared to the inhibition obtained using S1-IA or S1S2-IA. As shown, this peptide gave more inhibition than the two IA.

It should be noted that the synthetic peptide was both myristoylated and purified. Its sequence was based on another serotype of HBV (ayw) and differs in sequence from that used both for the IA and for the assembly of infectious HDV (adw2).

In addition, experiments were designed to examine whether addition of the inhibitors not only at the time of infection but also during 30 minutes prior to infection, would increase the level of inhibition. As summarized in FIG. 4B, the pretreatment with S1S2-IA did not significantly increase the level of inhibition relative to cells that were not pretreated.

In parallel with the experiment shown in FIG. 4B, experiments were designed to determined whether S1S2-IA would also act on HBV infection. The results as summarized in FIG. 4C show that there was inhibition. Moreover, the results were not significantly different from the inhibition observed for HDV infection. Without wishing to be bound by any particular theory, these results support the interpretation that HDV and HBV are using the same method of attachment and entry into susceptible cells.

Effects of Extent and Mode of Expression on S1S2-IA Secretion

The studies described herein showed that myristoylation was not needed for secretion. Also, the transfection procedure and the abundant intracellular expression, did not lead to the release of IA lacking preS1 sequences or of the host proteins hsc70 and beta-actin.

To test the possibility that over-expression of the preS sequences was somehow required for secretion, the amount of the S1S2-IA DNA construct used for transient transfection was decreased 64-fold. This reduced the protein expression by 20-fold and yet the observed secretion was still >80% (Table 2).

As an additional approach to exclude the possibility that the transient transfection procedure contributed to the observed secretion, a stable T-REx 293 cell line, containing a single copy of the S1S2-IA sequence per cell was established with expression under TET-on control (Chang, et al., 2005, J. Virol., 79:8182-8188). It was observed that secretion was >80% (Table 2). Similar results were obtained with a cell line expressing S1-IA. The results with the stable cell line demonstrate that in the absence of a transfection procedure, IA was efficiently secreted. A separate advantage of the cell line is that it provides a stable source of secreted IA.

TABLE 2

Effect of the S1S2-IA expression level on secretion.

| Mechanism for achieving IA expression[a] | Secretion (%) | Concentration In media[b] (nM) |
|---|---|---|
| Transient transfection with 10 μg plasmid | 95 | 540 |
| Transient transfection with 0.16 μg plasmid | 83 | 26 |
| Induced expression from stable cell line | 82 | 320 |

[a]Transient transfection of 293T cells was with plasmid expressing S1S2-IA. The stable cell line was T-Rex 293 containing a single copy of the S1S2-IA cDNA under control of a tetracycline inducible promoter.

[b]These were determined as in FIG. 2, an measured 2 days after either transfection or tetracycline induction.

Immunoadhesins Containing PreS Domains of HBV Large Envelope Protein are Secreted and Inhibit Virus Infection The disclosure presented herein demonstrate the role of preS1 sequences in protein secretion and therapeutic applications based on the observation that an IA containing preS1 sequences, such as S1-IA and S1S2-IA, are potent inhibitors of HDV and HBV infection.

Without wishing to be bound by any particular theory, it is believed that the preS1-directed protein secretion may have some significant differences relative to what happens when preS1, in the context of preS2 and S, translocates the ER membrane as part of the assembly and release of naturally-occurring forms that contain multimers, such as the empty virus-like particles or the nucleocapsid-containing HBV and HDV. A negative effect of multimerization is that in the absence of S, the L protein forms intracellular particles but they are not secreted (Xu, et al., 1997, J. Virol., 71:5487-5494).

It was determined that for the efficient secretion of IA, 30 amino acids from the N terminus of preS1 were both necessary and sufficient (Table 1). It is believed that this secretion signal was probably not cleaved off because N terminal myristoylation was detected on full-length IA (FIG. 3A) although myristoylation itself was not necessary for secretion (Table 1). HBV assembly and release is also not dependent upon myristoylation, even though this modification contributes to infectivity (Gripon, et al., 1995, Virology, 213:292-299).

It is believed that an asparagine at position 15 from the N terminus could be glycosylated (Bruss, et al., 1995, J. Virol., 69:6652-6657). The results presented herein demonstrate that mutating this amino acid led to no detectable change in secretion (Table 1), thus glycosylation, at least at this site, was not necessary for secretion. In addition, when tunicamycin was added soon after transient transfection, no inhibition of secretion was observably detected. This observation further supports the interpretation that no N-linked glycosylation was necessary for secretion. In addition, it was observed that over-expression of the IA did not contribute to the efficient secretion. This is because reducing the transient expression level by 20-fold or avoiding transfection and using inducible expression from an integrated cDNA, still yielded >80% secretion of the S1S1-IA (Table 2).

The mechanism of protein secretion can be divided into two major pathways: the classical ER/Golgi-dependent pathway and the unconventional pathway. Proteins using the classical pathway can translocate across the ER membrane either co-translationally or post translationally, largely dependent on whether a hydrophobic signal peptide is present (Kalies, et al., 1998, Eur. J. Biochem., 254:1-5). HBV preS lacks a predicted N terminal signal peptide. Also, the presence of myristoylation on preS (and the preS IA) argues against the removal of such a putative sequence. The preS is thought to translocate the ER membrane post-translationally (Bruss, et al., 1994, EMBO J., 13:2273-2279, Ostapchuk, et al., 1994, EMBO J., 13:1048-1057, Prange, et al., 1995, EMBO J., 14:247-256). Accordingly, preS IA is believed to be secreted through post-translational translocation into the ER lumen. A low level of IA dimerization was observed but its relation to translocation into an ER sub-domain with reduced oxidation activity was not determined. Nonetheless, an alternative secretory pathway of preS IA may be direct translocation across the plasma membrane via an unconventional pathway. Proteins using this pathway lack a typical signal peptide and are secreted through various mechanisms (Nickel, 2003, Eur. J. Biochem., 270:2109-2119). Although very limited information is available about motifs directing unconventional protein secretion, a few of such sequences have been determined. They do not share homology but most of them are located at the N terminus. One of them, like the preS1, is myristoylated at a glycine residue in position 2 (Denny, et al., 2000, J. Biol. Chem., 275:11017-11025). It is believed that the HBV preS secretion signal may functionally replace those motifs in directing protein secretion.

Relevant to the secretion mechanism and its regulation is that one or more host chaperones may bind to the short preS1 region. One candidate comes from a recent report that the HBV preS1 domain interacts with nascent polypeptide-associated complex alpha polypeptide (alpha-NAC) (Li, et al., 2005, Digestive Diseases and Sciences, 50:1156-1160). This protein is known to form a tight dimer with a second protein, alpha-NAC, binds to ribosomes and makes the first contact in the cytosol of nascent polypeptide chains. It can contribute to whether proteins lacking a signal sequence do or do not become targeted to the ER (Beatrix, et al., 2000, J. Biol. Chem., 275:37838-37845). A second candidate is hsc70 which is known to act as a cytosolic chaperone for preS (Lambert, et al., 2003, Proc. Natl. Acad. Sci., USA 100:5199-

5204, Loffler-Mary, et al., 1997, Virology, 235:144-152). Without wishing to be bound by any particular theory, in the event that preS IA actually enters the ER, then another candidate interacting protein is BiP, a resident ER chaperone, for which there is already evidence that it binds to HBV preS1 (Cho, et al., 2003, J. Virol., 77:2784-2788, Ryu, et al., 2000, J. Virol., 74:110-116).

The results presented herein demonstrate the therapeutic applications of such secreted IA species that can inhibit HDV infection (FIG. 4) and is applicable for inhibiting HBV infection. One such application is to use the compositions comprising preS1 in combination with existing anti-viral therapy. For example, while nucleoside inhibitors such as Entecavir (Baraclude, manufactured by Bristol-Myers Squibb) can suppress HBV levels in serum of patients chronically infected with HBV by 100,000-fold (Schreibman, et al., 2006, Future Virol., 1:541-552), the infection is nevertheless not cleared and drug resistance mutants can emerge over time (Revill, et al., 2006, Future Virol., 1:349-360). The IAs described elsewhere herein are based on fusions to a rabbit immunoglobulin, that can readily be changed to a human sequence. As disclosed elsewhere herein, the HBV IA are secreted efficiently (FIG. 2, Table 1) and are biologically active without further purification (FIG. 4). Therefore, as part of an anti-viral therapy, the IA could be purified in a single step of protein A binding and elution. Alternatively the IA could be delivered indirectly, for example, from a cDNA construct or expressed from a viral vector, such as a lentivirus (Levine, et al., 2006, Proc. Natl. Acad Sci., USA 103:17373-17377) or adeno-associated virus (Grimm, et al., 2006, J. Virol., 80:426-439).

Short myristoylated preS1 peptides have already been shown by others to inhibit infection of hepatocytes by HBV and HDV (Engelke, et al., 2006, Hepatology, 43:750-760, Gripon, et al., 2005, J. Virol., 79:1613-1622). However, the results presented herein demonstrate that at least S1-IA, S1S2-IA and S1S2 were secreted from a host cell and capable of inhibiting HDV infection. Accordingly the preS1 compositions of the invention is also applicable to inhibiting HBV infection.

In some instances, steric hindrance can apply to the IA constructs discussed herein. For example, it was observed that the 59 amino acids from the N terminus of preS1 when fused to IA were efficiently secreted but exhibited a less inhibition to HDV infection. It is believed that the lowered inhibition of virus infection may be a consequence of the Fc domain interfering with the access of the N terminal inhibitory sequence to the host receptor(s). It is also possible that the decrease in the ability to inhibit virus infection by the compositions discussed elsewhere herein associated with added size of the IA may be a decreased accessibility to target receptor(s), either at the surface of the host cell or even within some endosomal compartment.

Example 2

Lentivirus Vectors Carrying Hepatitis B Virus Antigens

The experiments disclosed herein describe a method of constructing a composition consisting of a lentiviral pseudotype expressing a heterogenous phenotype comprising envelope proteins derived from HBV. The results disclosed herein demonstrate that the cells transfected with the pseudovirus components do express both HIV and HBV surface proteins in FACS assays. In addition, the present invention discloses that the materials and methods disclosed herein are able to efficiently infect human hepatocytes.

The materials and methods employed in the experiments disclosed herein are now described.

Cells and Viruses

Human embryonic kidney 293T and T-REx cells, and human hepatoblastoma Huh7 cells, were grown in Dulbecco's modified Eagle's media supplemented with 10% fetal calf serum. Primary human hepatocytes in 48-well configuration plated as confluent monolayers on rat-tail collagen were obtained commercially (Admet, Cambrex, or CellzDirect) and maintained in Hepatostim medium supplemented with 0.01 mg/ml epidermal growth factor, receptor grade, both from BD Biosciences. All cells were maintained at 37° C. in 5% $CO_2$.

Packaging and Transfer Vector Constructs

The pCMVΔ8.2 HIV-1 Gag-Pol packaging construct (Naldini et al. Science 272:263-267, 1996) contains all HIV-1 genes except env, which encodes the envelope glycoproteins, and nef. pSV45H contains the whole pre-S1, pre-S2 and S open reading frames for all three HBV surface proteins as well as the HBV polyadenylation site under transcriptional control of a simian virus 40 early promoter (Persing et al. Science 234:1388-1391; 1986). pHXCMVlacZWP provides the reporter gene.

Production and Detection of Pseudo-Particles

To generate HBV pseudo-particles, 293T cells were transfected with expression vectors encoding the viral components and reporter gene. In brief, the Gag-Pol packaging construct (10 μg), the transfer vector (20 μg) and the HBV envelope protein expression construct (30 μg) were transfected into about 12 million 293T cells plated the day before per 10 cm culture plate using a calcium phosphate transfection protocol. Sodium butyrate is used to enhance the efficiency of transfection and expression by increasing enhancer-dependent transcription of inserts driven by the SV40 early promoter present in any pSV plasmid. Treatment of transfected cells with sodium butyrate can result in: a 2-3 fold increase in the number of cells able to express the insert; a 10-30 fold increase in the number of stable transfected colonies. The medium was replaced 16 hours after transfection. Supernatants containing the pseudo-viral particles were harvested 24 hours later, filtered through a 0.45 μm pore-sized membrane to clear cellular debris and used to transfect hepatocytes, RNA genome preparation, real-time RT-PCR quantitation, ultracentrifugation/concentration and Western blot analysis. Hepatocytes were harvested for Western, RT-PCR and subjected to fluorescence activated cell sorter (FACS) analysis.

The results of the experiments presented in this Example are now described.

Design of Lentivirus HBV Pseudovirus

Figure 5:
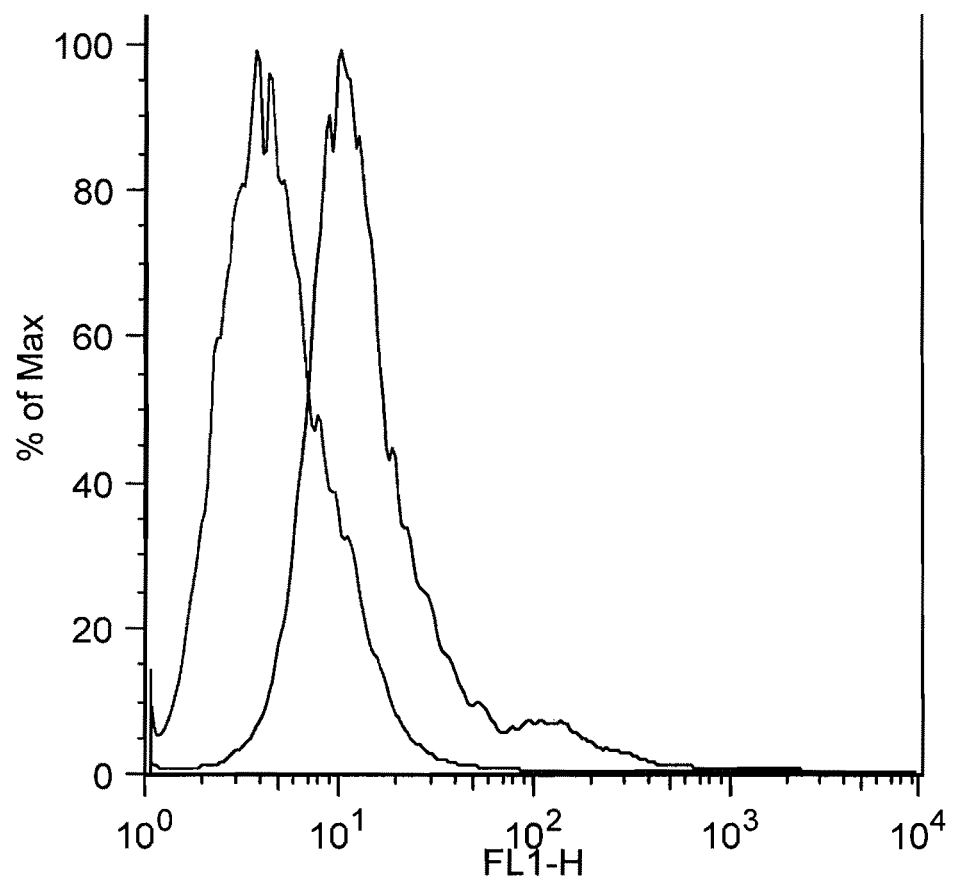

The result presented in this example involves the creation of a pseudovirus. These are a modified lentivirus with an HIV-based reporter genome that is replication defective and expresses a reporter protein such a green fluorescent protein (GFP) or LacZ. The genome is designed so that it only expresses the reporter protein to detect the one-round "dead end" infection mediated by the HBV surface proteins. 293T, a line of human embryonic kidney cells, are transfected with multiple vectors: pCMVΔ8.2 HIV-1 Gag-Pol packaging construct (Naldini et al. Science 272:263-267, 1996) contains all HIV-1 genes except env, which encodes the envelope glycoproteins, and nef; pSV45H contains the whole pre-S1, pre-S2 and S open reading frames for all three HBV surface proteins as well as the HBV polyadenylation site under transcriptional control of a simian virus 40 early promoter (Persing et al. Science 234:1388-1391; 1986); and, pHXCMVlacZWP provides the reporter gene FACS analysis detected surface expression of HBV proteins on the surface of harvested cells (FIG. 5).

Real time PCR demonstrated deduced titres of more than $10^8$ genomes per ml of harvested medium.

Infection of Primary Human Hepatocytes with Lentivirus HBV Pseudovirus

Figure 6:
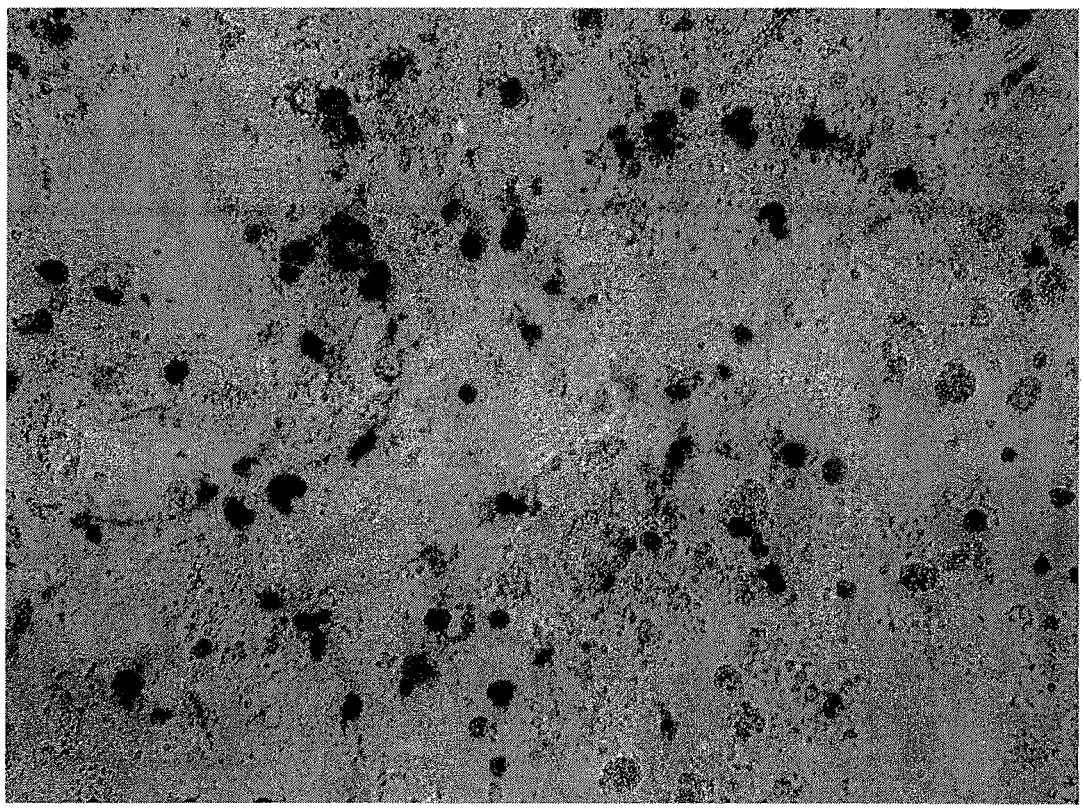
Figure 7:
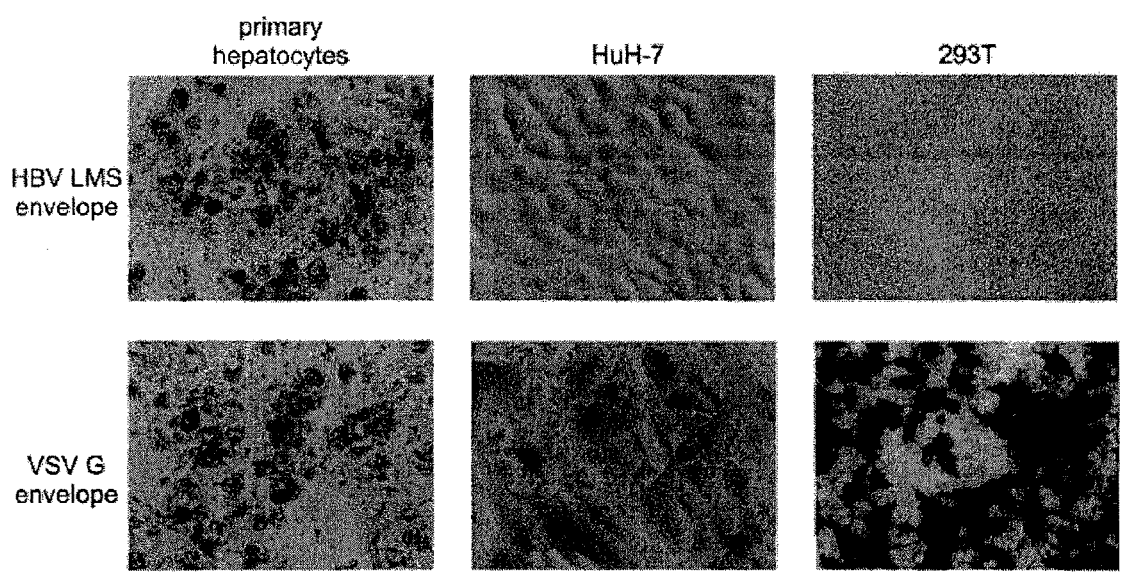

The media containing released virus particles are infectious to primary human hepatocytes without purification or concentration. With a multiplicity of infection (MOI: ratio of virus particles to number of cells being infected) of about 100, 40% of primary cultured human hepatocytes expressed the blue color indicating successful infection by the virus (FIG. 6 and FIG. 7).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed:

1. A secreted recombinant polypeptide comprising a preS1 region, wherein the preS1 region consists of the first 30 contiguous amino acids of the sequence of preS1 region of the adw2 serotype of HBV (SEQ ID NO: 2), wherein the polypeptide is capable of inhibiting HBV and/or HDV infection of hepatocytes, further wherein the polypeptide does not contain amino acids of the sequence of the S region of HBV.

2. The polypeptide of claim 1, wherein the virus infection is by HBV.

3. The polypeptide of claim 1, wherein the virus infection is by HBV and HDV.

4. The polypeptide of claim 1, wherein the 30 contiguous amino acids include the first 30 amino acids of preS1 region of HBV.

5. The polypeptide of claim 1, wherein the sequence of preS1 is fused to a constant domain sequence of an immunoglobulin.

6. The polypeptide of claim 5, wherein the immunoglobulin is selected from the group consisting of IgG-1, IgG-2, IgG-3, IgG-4, IgA, IgE, IgD, and IgM.

7. The polypeptide of claim 1, wherein the sequence of preS1 is fused to a sequence of preS2 region of HBV, thereby forming a polypeptide designated as S1S2.

8. The polypeptide of claim 7, wherein the S1S2 polypeptide is further fused to an immunoglobulin sequence.

9. The polypeptide of claim 1, wherein the polypeptide is myristoylated.

10. A method of in vivo inhibition of hepatocyte infection, the method comprising administering to an animal in need thereof an effective amount of an isolated nucleic acid sequence encoding a secreted fusion polypeptide comprising: 1) a preS1 region, wherein the preS1 region consists of the first 30 contiguous amino acids of the sequence of preS1 region of the adw2 serotype of HBV (SEQ ID NO: 2); and 2) a constant domain sequence of an immunoglobulin or a sequence of preS2 region of HBV, wherein the polypeptide is capable of inhibiting HBV and/or HDV virus infection of hepatocytes.

11. The method of claim 10, wherein the hepatocyte infection is by HBV.

12. The method of claim 10, wherein the hepatocyte infection is by HBV and HDV.

13. The method of claim 10, wherein the sequence of preS1 is fused to a constant domain sequence of an immunoglobulin.

14. The method of claim 13, wherein the immunoglobulin is selected from the group consisting of IgG-1, IgG-2, IgG-3, IgG-4, IgA, IgE, IgD, and IgM.

15. The method of claim 10, wherein the sequence of preS1 is fused to a sequence of preS2 region of HBV, thereby forming a polypeptide designated as S1S2.

16. The method of claim 15, wherein the S1S2 polypeptide is further fused to an immunoglobulin sequence.

17. The method of claim 10, wherein the polypeptide is myristoylated.

18. An isolated polynucleotide encoding a polypeptide comprising a preS1 region, wherein the preS1 region consists of the first 30 contiguous amino acids of the sequence of preS1 region of the adw2 serotype of HBV (SEQ ID NO: 2), wherein the polypeptide is capable of inhibiting HBV and/or HDV virus infection of hepatocytes, further wherein the polypeptide does not contain amino acids of the sequence of the S region of HBV.

19. A method of in vivo inhibition of hepatocyte infection, the method comprising administering to an animal in need thereof an effective amount of an isolated secreted fusion polypeptide comprising: 1) a preS1 region, wherein the preS1 region consists of the first 30 contiguous amino acids of the sequence of preS1 region of the adw2 serotype of HBV (SEQ ID NO: 2); and 2) a constant domain sequence of an immunoglobulin or a sequence of preS2 region of HBV, wherein the polypeptide is capable of inhibiting HBV and/or HDV virus infection of hepatocytes.

* * * * *

UNITED STATES PATENT AND TRADEMARK OFFICE
CERTIFICATE OF CORRECTION

| | | |
|---|---|---|
| PATENT NO. | : 8,748,373 B2 | Page 1 of 1 |
| APPLICATION NO. | : 12/526759 | |
| DATED | : June 10, 2014 | |
| INVENTOR(S) | : Ning Chai and John M. Taylor | |

It is certified that error appears in the above-identified patent and that said Letters Patent is hereby corrected as shown below:

In the Specification

Column 1, Line 16 should read as follows:
STATEMENT REGARDING FEDERALLY SPONSORED RESEARCH OR DEVELOPMENT
This invention was made with government support under U01 AI058269 awarded by the National Institutes of Health. The government has certain rights in the invention.

Signed and Sealed this
Twelfth Day of September, 2023

Katherine Kelly Vidal
*Director of the United States Patent and Trademark Office*

SEQUENCE LISTING

```
<160> NUMBER OF SEQ ID NOS: 7

<210> SEQ ID NO 1
<211> LENGTH: 59
<212> TYPE: PRT
<213> ORGANISM: artificial sequence
<220> FEATURE:
<223> OTHER INFORMATION: 1-59 of HBV

<400> SEQUENCE: 1

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Ala Ala Asn Gln Val Gly
    50                  55

<210> SEQ ID NO 2
<211> LENGTH: 30
<212> TYPE: PRT
<213> ORGANISM: artificial sequence
<220> FEATURE:
<223> OTHER INFORMATION: 1-30 of HBV

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu
            20                  25                  30

<210> SEQ ID NO 3
<211> LENGTH: 10
<212> TYPE: PRT
<213> ORGANISM: artificial sequence
<220> FEATURE:
<223> OTHER INFORMATION: 1-10 of HBV

<400> SEQUENCE: 3

Met Gly Gly Trp Ser Ser Lys Pro Arg Lys
1               5                   10

<210> SEQ ID NO 4
<211> LENGTH: 145
<212> TYPE: PRT
<213> ORGANISM: artificial sequence
<220> FEATURE:
<223> OTHER INFORMATION: 1, 31-174 HBV

<400> SEQUENCE: 4
```

```
Met Asp Pro Ala Phe Gly Ala Asn Ser Asn Asn Pro Asp Trp Asp Phe
1               5                   10                  15

Asn Pro Ile Lys Asp His Trp Pro Ala Asn Gln Val Gly Val Gly
            20                  25                  30

Ala Phe Gly Pro Gly Leu Thr Pro Pro His Gly Gly Ile Leu Gly Trp
            35                  40                  45

Ser Pro Gln Ala Gln Gly Ile Leu Thr Thr Val Ser Thr Ile Pro Pro
50                  55                  60

Pro Ala Ser Thr Asn Arg Gln Ser Gly Arg Gln Pro Thr Pro Ile Ser
65                  70                  75                  80

Pro Pro Leu Arg Asp Ser His Pro Gln Ala Met Gln Trp Asn Ser Thr
                85                  90                  95

Ala Phe His Gln Ala Leu Gln Asp Pro Arg Val Arg Gly Leu Tyr Leu
            100                 105                 110

Pro Ala Gly Gly Ser Ser Ser Gly Thr Val Asn Pro Ala Pro Asn Ile
            115                 120                 125

Ala Ser His Ile Ser Ser Ile Ser Ala Arg Thr Gly Asp Pro Val Thr
            130                 135                 140

Asn
145

<210> SEQ ID NO 5
<211> LENGTH: 119
<212> TYPE: PRT
<213> ORGANISM: artificial sequence
<220> FEATURE:
<223> OTHER INFORMATION: G2A, G13A mutant

<400> SEQUENCE: 5

Met Ala Gly Trp Ser Ser Lys Pro Arg Lys Gly Met Ala Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
            35                  40                  45

Lys Asp His Trp Pro Ala Ala Asn Gln Val Gly Val Gly Ala Phe Gly
50                  55                  60

Pro Gly Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala
            115

<210> SEQ ID NO 6
<211> LENGTH: 119
<212> TYPE: PRT
<213> ORGANISM: artificial sequence
<220> FEATURE:
<223> OTHER INFORMATION: N15Q mutant

<400> SEQUENCE: 6

Met Gly Gly Trp Ser Ser Lys Pro Arg Lys Gly Met Gly Thr Gln Leu
1               5                   10                  15

Ser Val Pro Asn Pro Leu Gly Phe Phe Pro Asp His Gln Leu Asp Pro
            20                  25                  30
```

Ala Phe Gly Ala Asn Ser Asn Pro Asp Trp Asp Phe Asn Pro Ile
            35                  40                  45

Lys Asp His Trp Pro Ala Ala Asn Gln Val Gly Val Gly Ala Phe Gly
 50                      55                  60

Pro Gly Leu Thr Pro Pro His Gly Gly Ile Leu Gly Trp Ser Pro Gln
 65              70                  75                  80

Ala Gln Gly Ile Leu Thr Thr Val Ser Thr Ile Pro Pro Pro Ala Ser
                 85                  90                  95

Thr Asn Arg Gln Ser Gly Arg Gln Pro Thr Pro Ile Ser Pro Pro Leu
             100                 105                 110

Arg Asp Ser His Pro Gln Ala
            115

<210> SEQ ID NO 7
<211> LENGTH: 400
<212> TYPE: PRT
<213> ORGANISM: Hepatitis B virus

<400> SEQUENCE: 7

Met Gly Gly Trp Ser Ser Lys Pro Arg Lys Gly Met Gly Thr Asn Leu
 1               5                  10                  15

Ser Val Pro Asn Pro Leu Gly Phe Phe Pro Asp His Gln Leu Asp Pro
                 20                  25                  30

Ala Phe Gly Ala Asn Ser Asn Asn Pro Asp Trp Asp Phe Asn Pro Ile
            35                  40                  45

Lys Asp His Trp Pro Ala Ala Asn Gln Val Gly Val Gly Ala Phe Gly
 50                      55                  60

Pro Gly Leu Thr Pro Pro His Gly Gly Ile Leu Gly Trp Ser Pro Gln
 65              70                  75                  80

Ala Gln Gly Ile Leu Thr Thr Val Ser Thr Ile Pro Pro Pro Ala Ser
                 85                  90                  95

Thr Asn Arg Gln Ser Gly Arg Gln Pro Thr Pro Ile Ser Pro Pro Leu
             100                 105                 110

Arg Asp Ser His Pro Gln Ala Met Gln Trp Asn Ser Thr Ala Phe His
            115                 120                 125

Gln Ala Leu Gln Asp Pro Arg Val Arg Gly Leu Tyr Leu Pro Ala Gly
        130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
            210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

-continued

| | | | | | | | | | | | | |
|---|---|---|---|---|---|---|---|---|---|---|---|---|
|Thr|Thr 290|Ser|Thr|Gly|Pro|Cys 295|Lys|Thr|Cys|Thr 300|Pro|Ala|Gln|Gly|
|Asn 305|Ser|Met|Phe|Pro|Ser 310|Cys|Cys|Cys|Thr|Lys 315|Pro|Thr|Asp|Gly|Asn 320|
|Cys|Thr|Cys|Ile|Pro 325|Ile|Pro|Ser|Ser|Trp 330|Ala|Phe|Ala|Lys|Tyr 335|Leu|
|Trp|Glu|Trp|Ala|Ser 340|Val|Arg|Phe|Ser 345|Trp|Leu|Ser|Leu|Leu 350|Val|Pro|
|Phe|Val|Gln 355|Trp|Phe|Val|Gly|Leu 360|Ser|Pro|Thr|Val|Trp 365|Leu|Ser|Ala|
|Ile|Trp 370|Met|Met|Trp|Tyr|Trp 375|Gly|Pro|Ser|Leu|Tyr 380|Ser|Ile|Val|Ser|
|Pro 385|Phe|Ile|Pro|Leu|Leu 390|Pro|Ile|Phe|Phe|Cys 395|Leu|Trp|Val|Tyr|Ile 400|